US010921309B2

(12) United States Patent
Movileanu et al.

(10) Patent No.: US 10,921,309 B2
(45) Date of Patent: Feb. 16, 2021

(54) SINGLE-MOLECULE PORE-BASED SENSOR FOR PROTEINS AND TRANSIENT PROTEIN-PROTEIN INTERACTIONS

(71) Applicants: Liviu Movileanu, Jamesville, NY (US); Avinash Kumar Thakur, Syracuse, NY (US)

(72) Inventors: Liviu Movileanu, Jamesville, NY (US); Avinash Kumar Thakur, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 1 day.

(21) Appl. No.: 16/177,554

(22) Filed: Nov. 1, 2018

(65) Prior Publication Data

US 2019/0128867 A1    May 2, 2019

Related U.S. Application Data

(60) Provisional application No. 62/579,982, filed on Nov. 1, 2017, provisional application No. 62/720,190, filed on Aug. 21, 2018.

(51) Int. Cl.
| | |
|---|---|
| *G01N 33/487* | (2006.01) |
| *G01N 33/68* | (2006.01) |
| *G01N 33/566* | (2006.01) |
| *G01N 33/92* | (2006.01) |
| *B82Y 40/00* | (2011.01) |
| *B82Y 30/00* | (2011.01) |

(52) U.S. Cl.
CPC ..... *G01N 33/48721* (2013.01); *G01N 33/566* (2013.01); *G01N 33/6818* (2013.01); *G01N 33/6872* (2013.01); *G01N 33/92* (2013.01); *B82Y 30/00* (2013.01); *B82Y 40/00* (2013.01)

(58) Field of Classification Search
None
See application file for complete search history.

(56) References Cited

U.S. PATENT DOCUMENTS

2012/0003694 A1*  1/2012  Movileanu ........... C07K 14/245
                                                                    435/69.1
2015/0080242 A1*  3/2015  Chen .................... C07K 14/245
                                                                    506/9

OTHER PUBLICATIONS

Mohammad et al., Redesign of a Plugged β-Barrel Membrane Protein, Journal of Biological Chemistry, vol. 286, No. 10, pp. 8000-8013. (Year: 2011).*

* cited by examiner

*Primary Examiner* — Melanie Brown
(74) *Attorney, Agent, or Firm* — Bond Schoeneck and King PLLC; David Nocilly; George McGuire

(57) ABSTRACT

A bioinspired protein pore-based nanostructure that can provide selective, real-time sampling of protein-protein interactions at single-molecule resolution. This modular nanostructure relied on a single polypeptide chain that encompassed a heavily truncated outer membrane protein, a highly flexible connector, a protein receptor element, as well as a polypeptide adapter. The presence of a protein ligand analyte in solution produced reversible binding and release events, in the form of discrete and stochastic current transitions between open substates of the transmembrane pore, the nature of which depend on both the amount of protein ligand analyte and the strength of the transient PPIs in aqueous phase.

13 Claims, 25 Drawing Sheets
Specification includes a Sequence Listing.

SINGLE-MOLECULE PORE-BASED SENSOR FOR PROTEINS AND TRANSIENT PROTEIN-PROTEIN INTERACTIONS

CROSS-REFERENCE TO RELATED APPLICATIONS

The present application claims priority to U.S. Provisional No. 62/579,982 filed on Nov. 1, 2017 and U.S. Provisional No. 62/720,190 filed on Aug. 21, 2018.

STATEMENT REGARDING FEDERALLY SPONSORED RESEARCH OR DEVELOPMENT

This invention was made with government support under Grant Nos. R01 GM088403 and R01 GM129429 awarded by the U.S. National Institutes of Health (NIH). The government has certain rights in the invention.

BACKGROUND OF THE INVENTION

1. Field of the Invention

The present invention relates to protein interaction sensors and, more particularly, to a protein pore-based nanostructure that provides selective, real-time sampling of transient protein-protein interactions at single-molecule resolution.

2. Description of the Related Art

Sequencing of the human genome ignited the extensive exploration of a large number of functional proteins involved in complex interactions with other proteins, initiating the mapping of interactome. In many cases, the physical associations of these proteins regulate critical features of the cell function under normal and pathogenic conditions, and therefore they might be used as strategic therapeutic targets. However, the quantitative and mechanistic understanding of transient protein-protein interactions (PPIs) is still in its infancy. There is a continual demand for the development of novel nanoproteomics approaches that should enable the acquisition of insightful kinetic information in a scalable fashion. In response to such a pressing problem, a modular protein pore-based nanostructure was designed for the selective, real-time examination of transient PPIs at single-molecule detail. The obvious advantage of single-molecule detection using nanopore sensors is their ability to be integrated into nanofluidic devices and in a high-throughput format. This development imposed two prerequisites. First, the transient PPIs needed to occur within aqueous phase, because the dimensions of folded proteins usually exceed those cross-sectional internal diameters of nanopores; thereby, they should be detected beyond the fundamental physical limit of single-molecule sensing when they partition into the nanopore interior. Second, a transducing mechanism was required, converting the reversible physical associations and dissociations of the two protein partners in aqueous phase into a high-fidelity electrical signature of the nanopore sensor.

BRIEF SUMMARY OF THE INVENTION

The present invention overcomes the challenges in the field by providing a modular protein-pore based protein sensor having a membrane, aa transducer positioned in the membrane, a protein receptor tethered to the transducer by a flexible linker, and a charged polypeptide adaptor coupled to the protein receptor. The protein receptor is tethered to the N terminus of the transducer. The transducer comprises a monomeric β-barrel scaffold derived from ferric hydroxamate uptake component A (FhuA) of $E.\ coli$. The membrane divides a chamber into a cis side and a trans side and the transducer is positioned in the membrane so that an N terminus and a C terminus of the transducer are positioned in the cis side of the chamber. The addition of a protein target that interacts with the protein receptor into the cis side of the chamber will produce a reversible current transition across the membrane. The reversible current transition across the membrane reflects an interaction between the protein receptor and the protein target and a concentration of the protein target. The reversible current transition may comprise a reduction in current flowing across the membrane when a predetermined voltage is established across the membrane.

The present invention also includes a method of detecting a protein-protein interaction, where the first step involves providing a protein sensor having a membrane dividing a chamber into a cis side and a trans side, a transducer positioned in the membrane so that an N terminus and a C terminus of the transducer is position in the cis side of the chamber, a protein receptor tethered to the N terminus of the transducer by a flexible linker, and a charged polypeptide adaptor coupled to the protein receptor. The second step is adding a protein target that will interact with the protein receptor into the cis side of the chamber. The last step is detecting whether there is a reversible current transition across the membrane in response to adding the protein target to the cis side of the chamber. The reversible current transition across the membrane reflects an interaction between the protein receptor and the protein target and a concentration of the protein target.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 7:
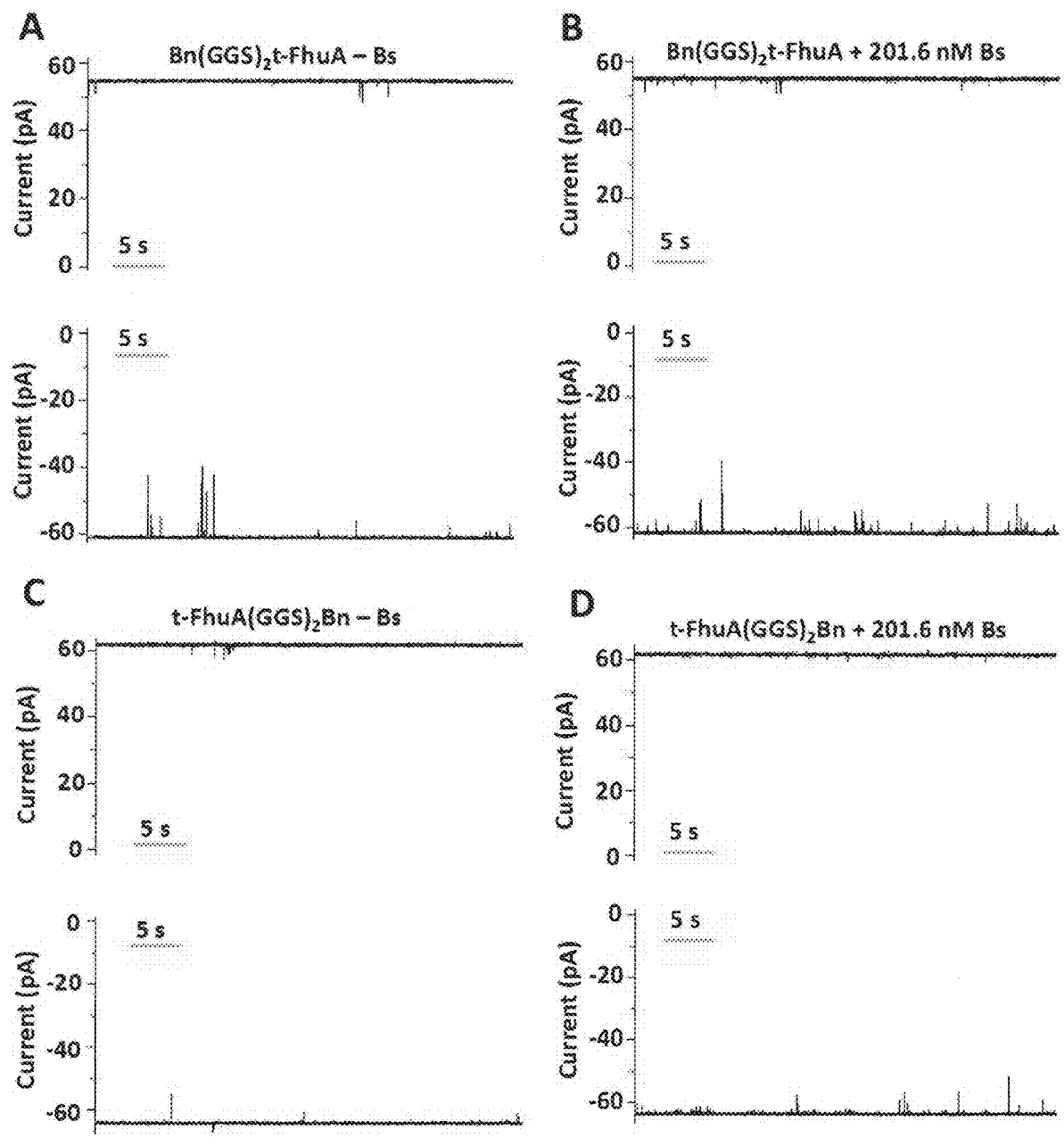
Figure 8:
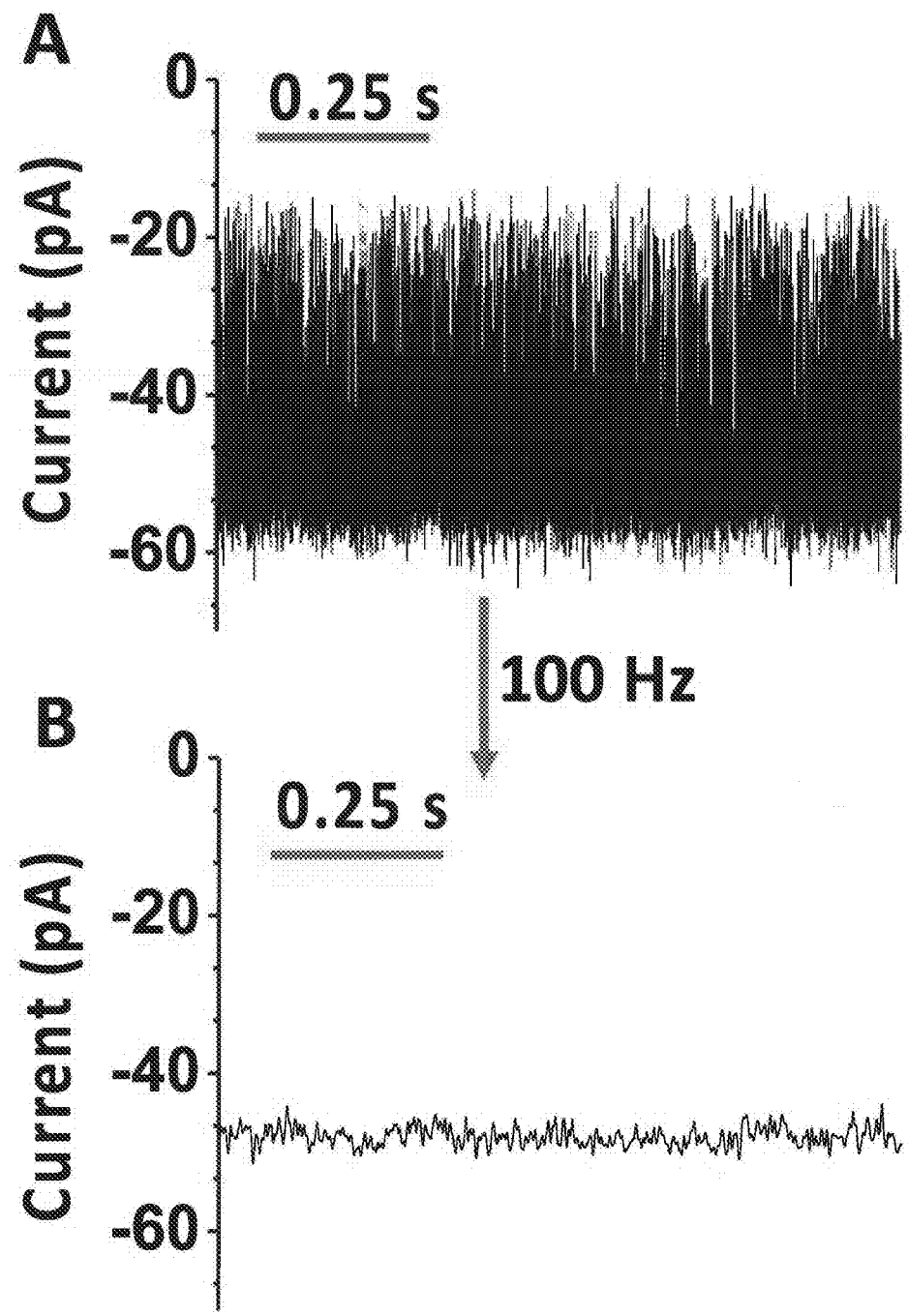
Figure 9:
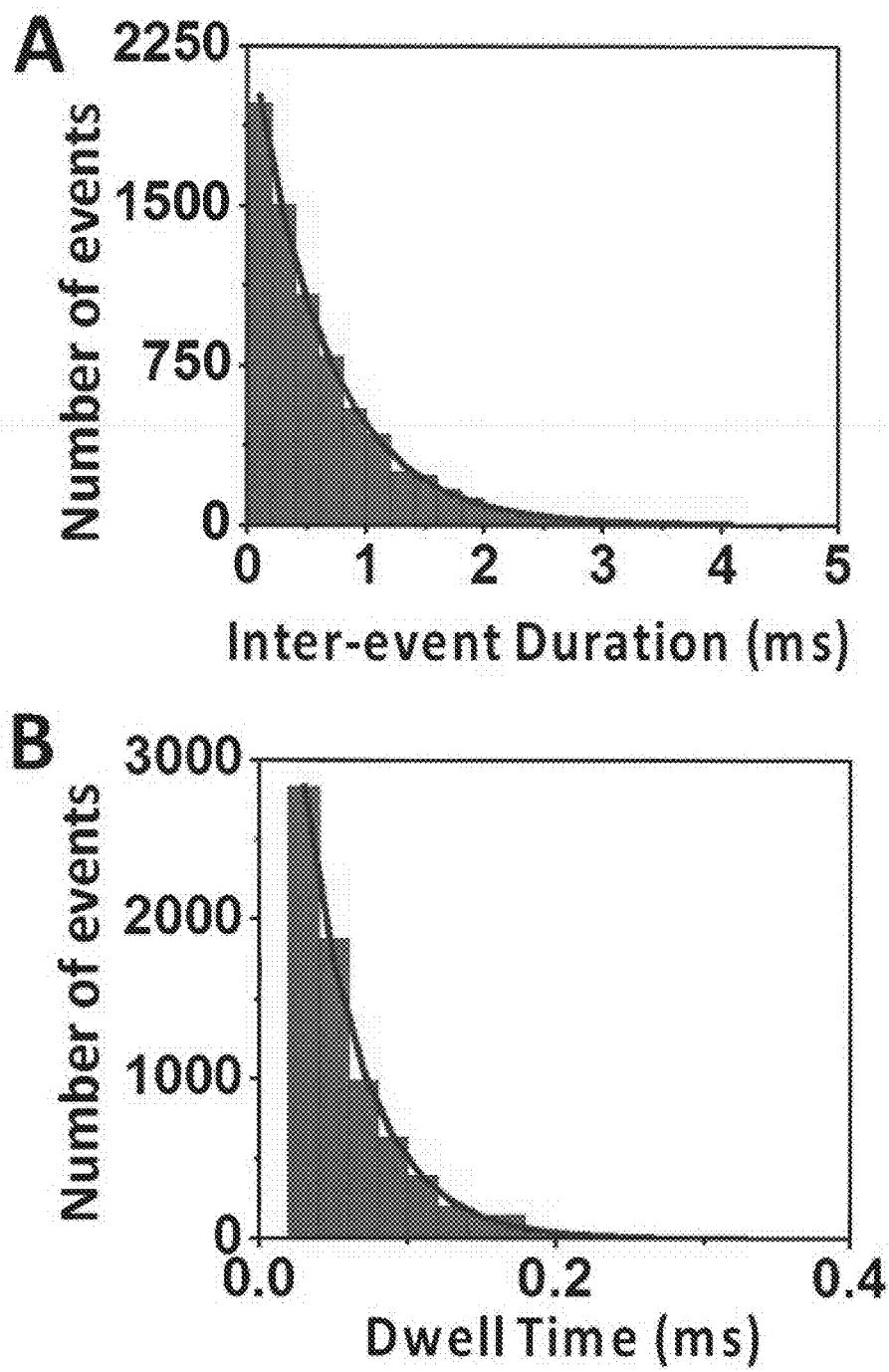
Figure 10:
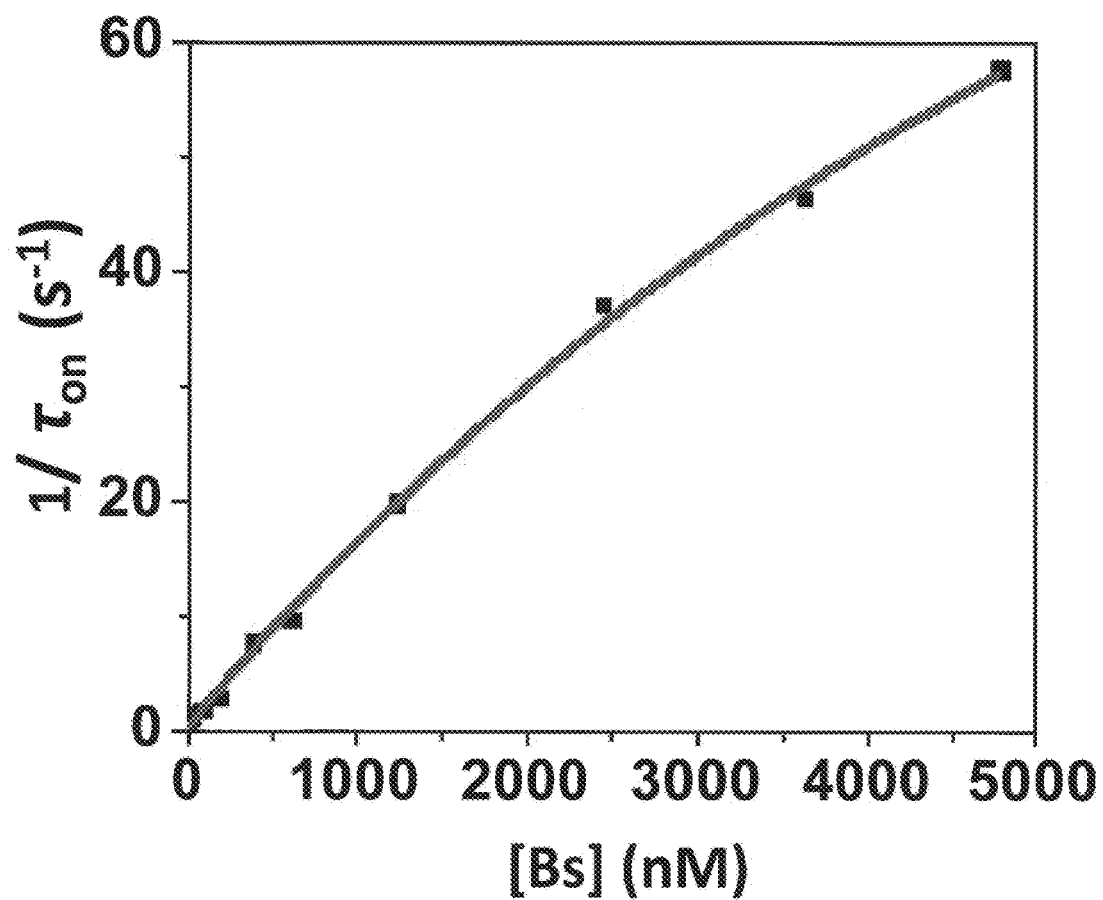
Figure 11:
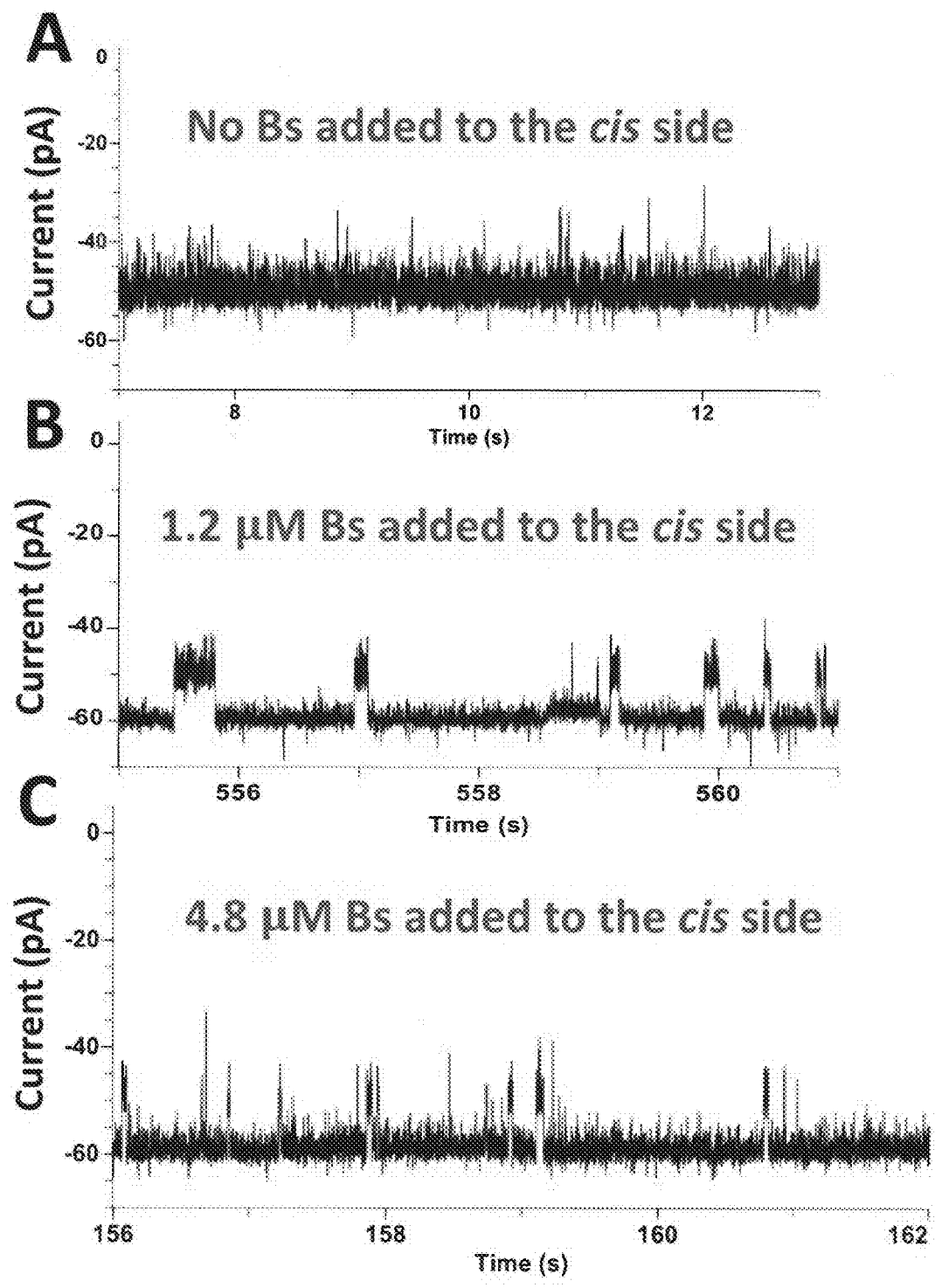
Figure 12:
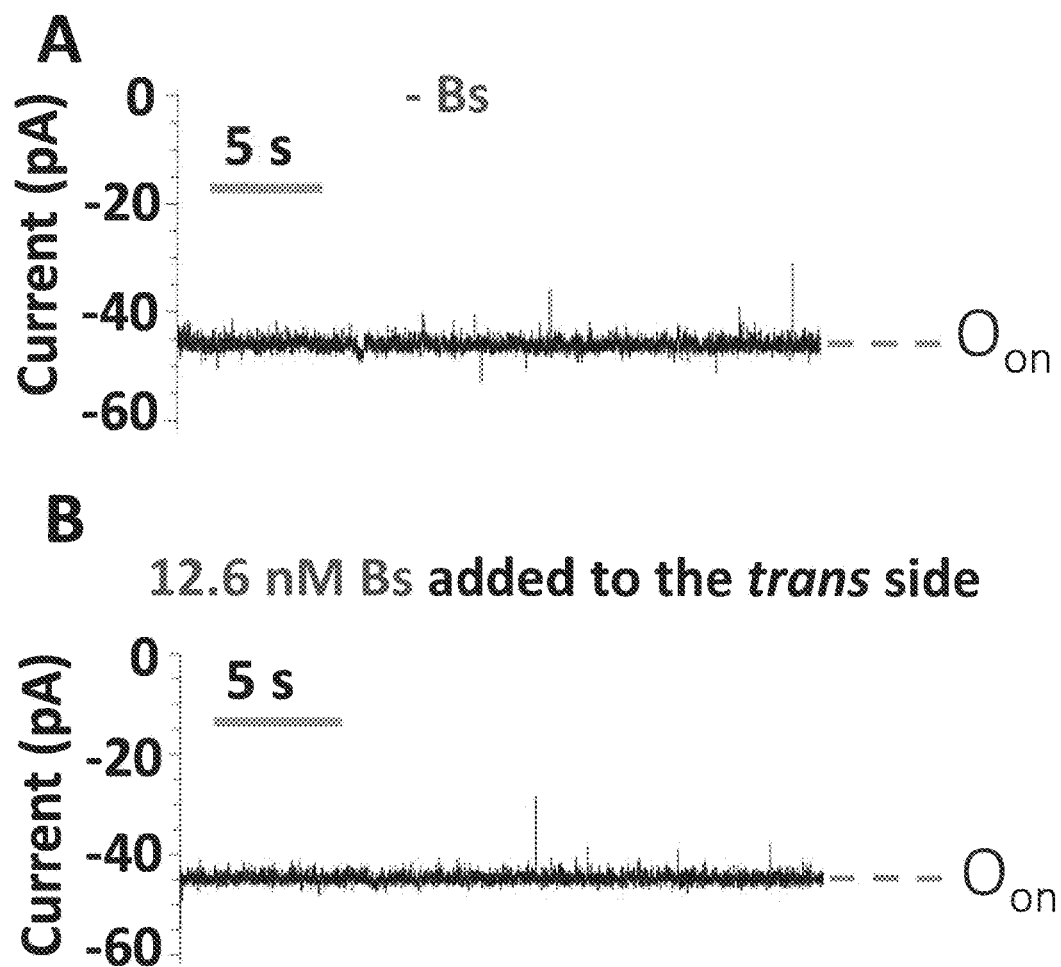

FIG. 7 is a series of graphs showing the lack of detectable binding Bn-Bs interactions when Bn(GGS)$_2$-containing t-FhuA pores were used. In graph (A) the single-channel electrical signature of the nanostructure when Bn(GGS)$_2$ was fused to the N-terminus of t-FhuA and no Bs was added to the cis side; In graph (B) the single-channel electrical signature of the nanostructure when Bn(GGS)$_2$ was fused to the N-terminus of t-FhuA and 201.6 nM Bs was added to the cis side; In graph (C) the single-channel electrical signature of the nanostructure when Bn(GGS)$_2$ was fused to the C-terminus of t-FhuA and no Bs was added to the cis side; In graph (D) the single-channel electrical signature of the nanostructure when Bn(GGS)$_2$ was fused to the C-terminus of t-FhuA and 201.6 nM Bs was added to the cis side. The top and bottom traces were acquired at transmembrane potentials of +40 and −40 mV, respectively. All recordings were performed in 300 mM KCl, 10 mM Tris.HCl, pH 8, at a temperature of 23±2° C. All traces were low-pass Bessel filtered at a frequency of 100 Hz;

FIG. 8 is a graph of the raw signal of the single-channel electrical recordings of OBn[GGS]$_2$t-FhuA, which was low-pass, 8-pole Bessel filtered at a frequency of 10 kHz. In graph (A) the unprocessed signal reveals fast flickering current blockades at a negative transmembrane potential; in graph (B) the signal was additionally filtered at 500 Hz. No long-lived current substates were noticed after this low-pass Bessel filtering, but a reduced current amplitude was observed as compared with that recorded with Bn[GGS]$_2$t-FhuA under similar experimental conditions. This current reduction was in the range 20-25% out of that recorded with Bn[GGS]$_2$t-FhuA. The applied transmembrane potential was −40 mV. The other experimental conditions were the same as in FIG. 2;

FIG. 9 is a series of representative dwell-time histograms of the inter-event duration and time constant of the short-lived downward current spikes recorded in FIG. 8. The inter-event duration was 1.0±0.4 ms, whereas the time constant was 30±14 ms (n=7);

FIG. 10 is a graph of the frequency of the binding Bn-Bs interactions recorded in a fairly broad range of the Bs concentration; and FIG. 11 is a series of graphs of the single-molecule determination of the kinetic rate constants of the PPI interactions at very high Bs concentrations added to the cis side of the chamber;

FIG. 12 is a pair of signal traces showing the addition of high-affinity Bs to the trans side has never produced long-lived current transitions when an OBn(GGS)$_2$t-FhuA nanopore was inspected, where trace (A) shows no Bs was added to the trans side and trace (B) shows 12.63 nM Bs added to the trans side.

Figure 13A:
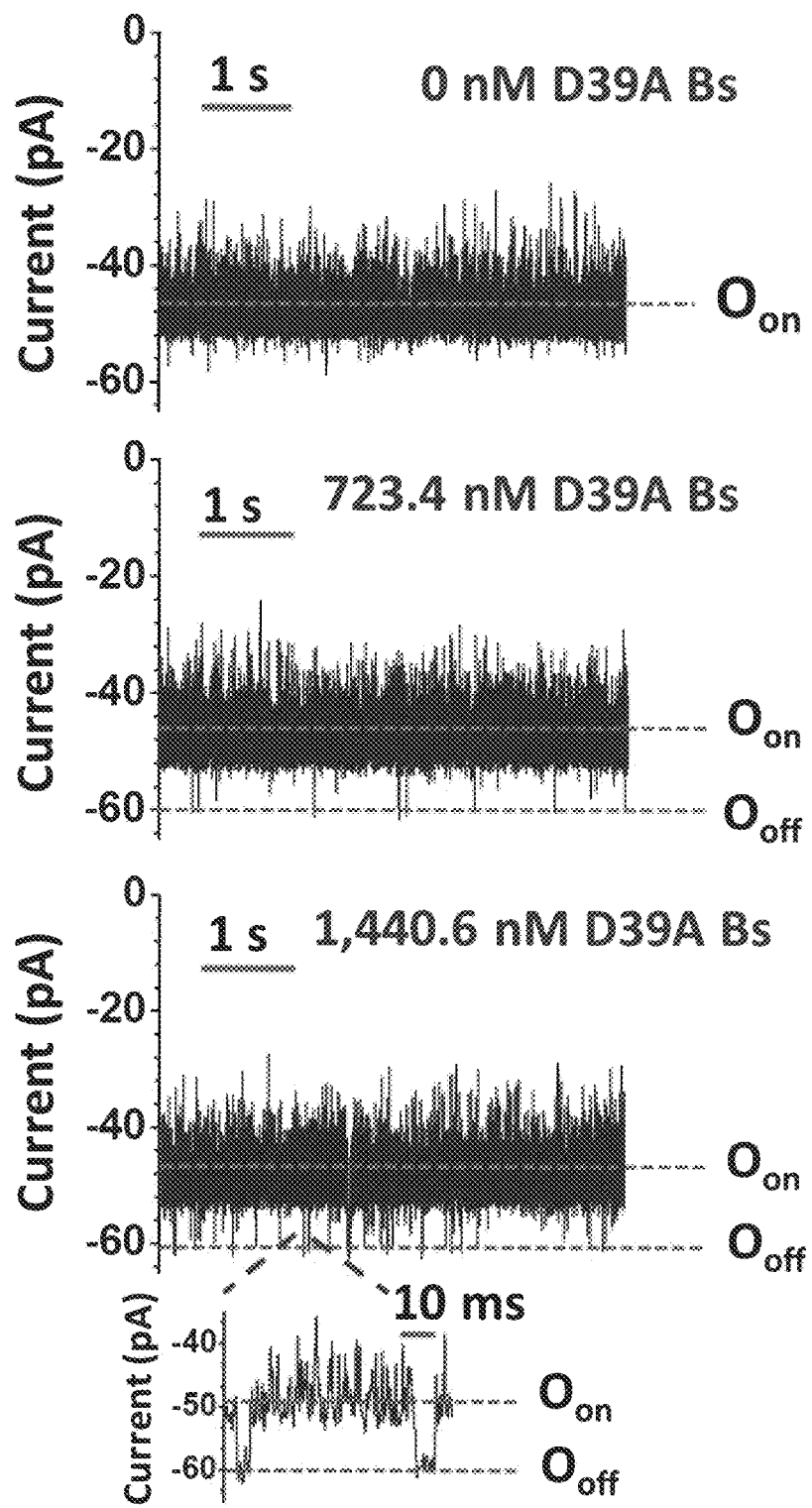
Figure 13B:
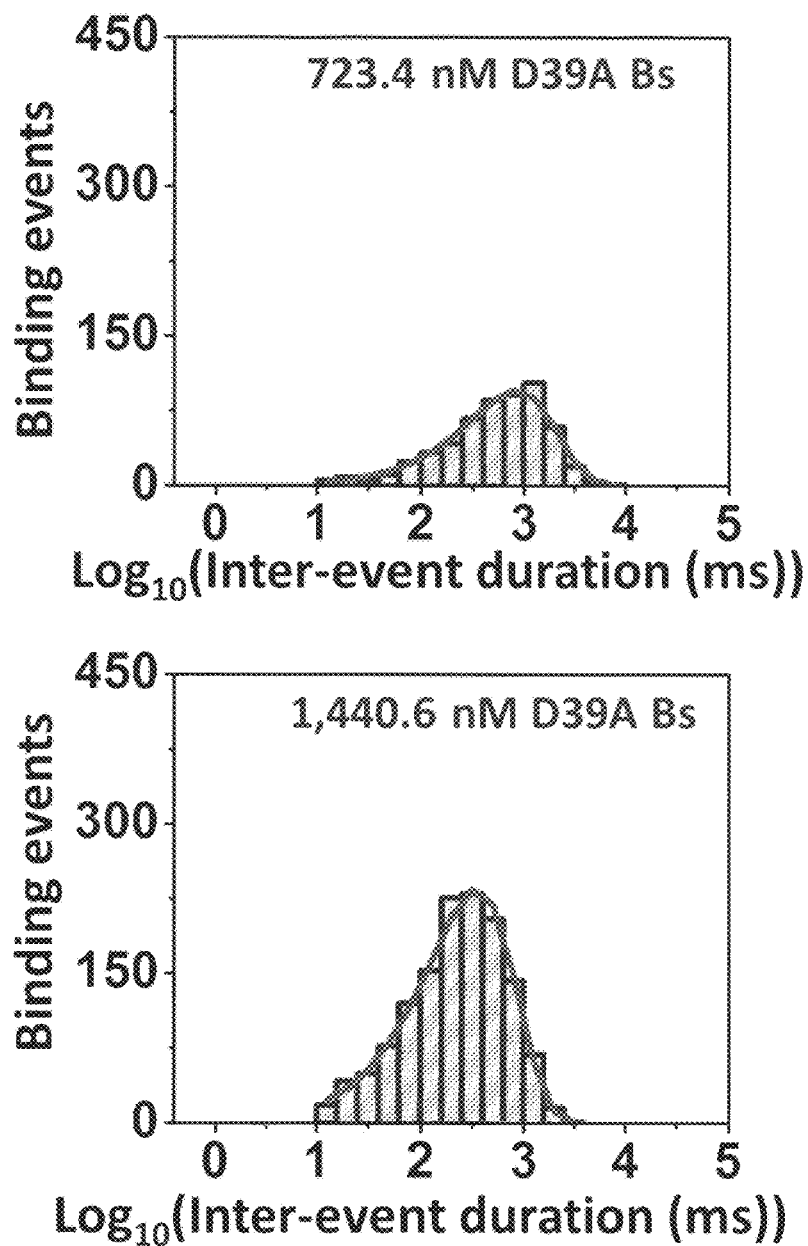
Figure 13C:
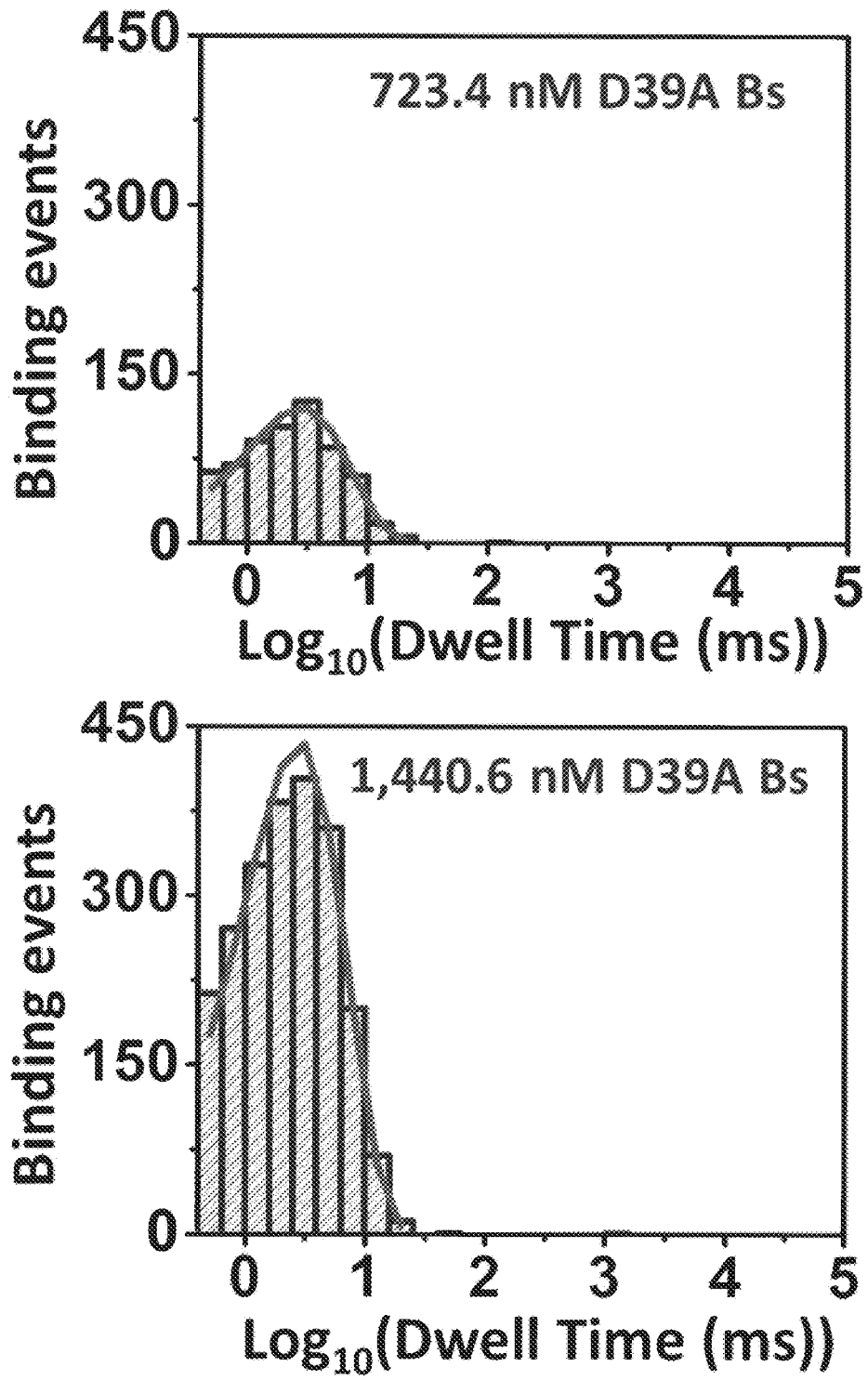
Figure 13D:
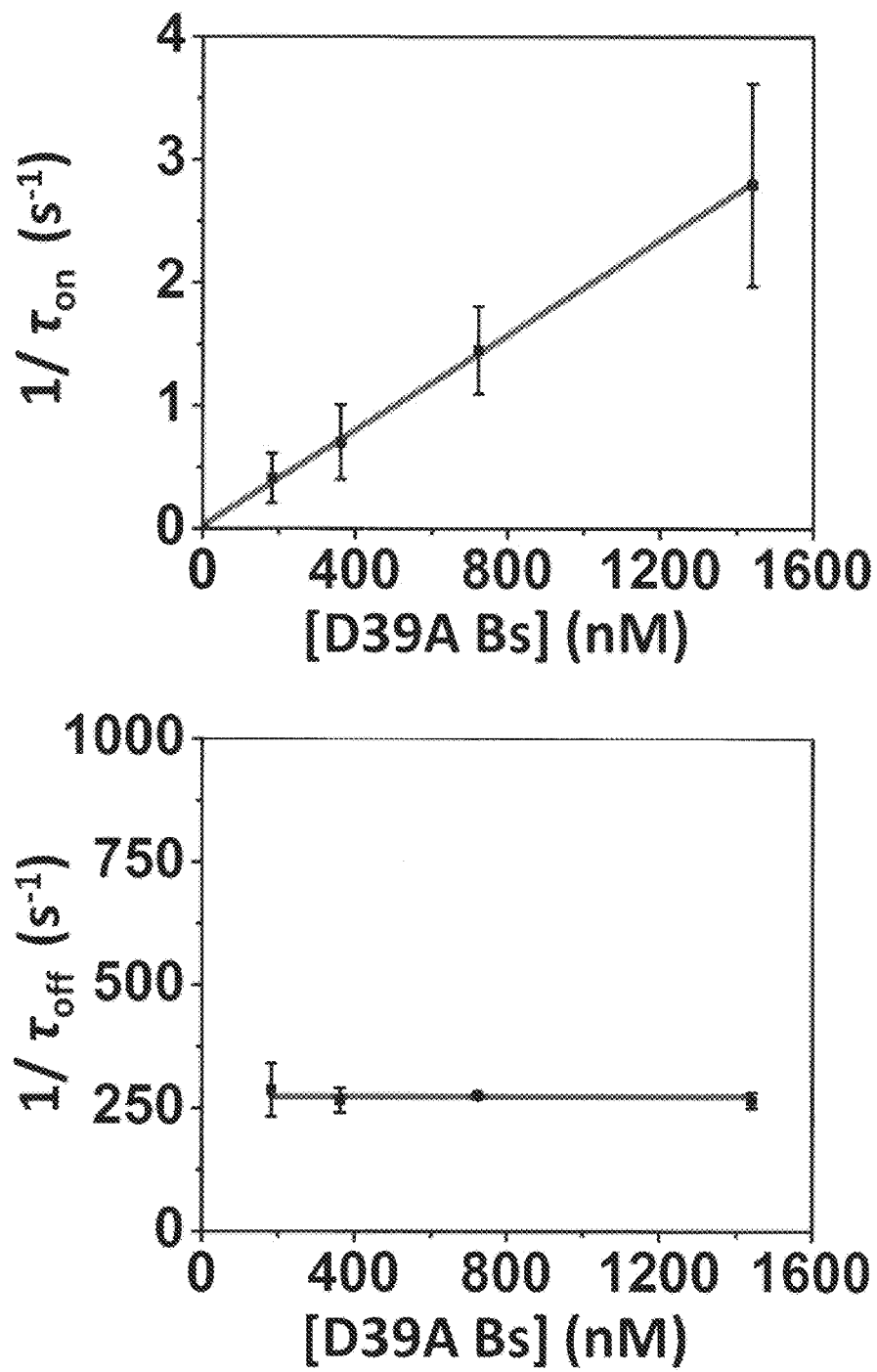

FIG. 13A is series of a graphs of representative single-molecule captures of transient PPI between Bn and D39A Bs using OBn(GGS)$_2$t-FhuA. The applied transmembrane potential was −40 mV. The low-affinity D39A Bs was added to the cis compartment. The current traces were low-pass Bessel filtered at 1 kHz;

FIG. 13B is a series of representative semi-logarithmic histograms of the inter-event duration, $\tau_{on}$, of the PPI at two D39A Bs concentrations. The fits were accomplished using a logarithm likelihood ratio (LLR) test. For a confidence level C=0.95, it was determined that the best model was one-exponential fit. The $\tau_{on}$ values were 855±1 and 378±12 ms at D39 Bs concentrations of 723.4 nM and 1,440.6 nM, respectively;

FIG. 13C is a series of representative semi-logarithmic event dwell-time histograms of the weak PPI at two D39A Bs concentrations. For a confidence level C=0.95, the best model was one-exponential fit. The $\tau_{off}$ values determined from these histograms were 3.6±0.2 ms and 3.6±0.1 ms at D39A Bs concentrations of 723.4 nM and 1,440.6 nM, respectively;

FIG. 13D is a series of diagrams illustrating the dependence of $1/\tau_{on}$ and $1/\tau_{off}$ on the D39A Bs concentration, [D39A Bs]. The slope of the linear fit of $1/\tau_{on}$ versus [D39A Bs] is the association rate constant, $k_{on}$, of the PPI, because $k_{on}=1/(\tau_{on}[D39A\ Bs])$. The bottom diagram shows that the $\tau_{off}$ binding time was independent of the D39A Bs concentration. Error bars represent the standard deviations of at least three distinct experiments.

Figure 14A:
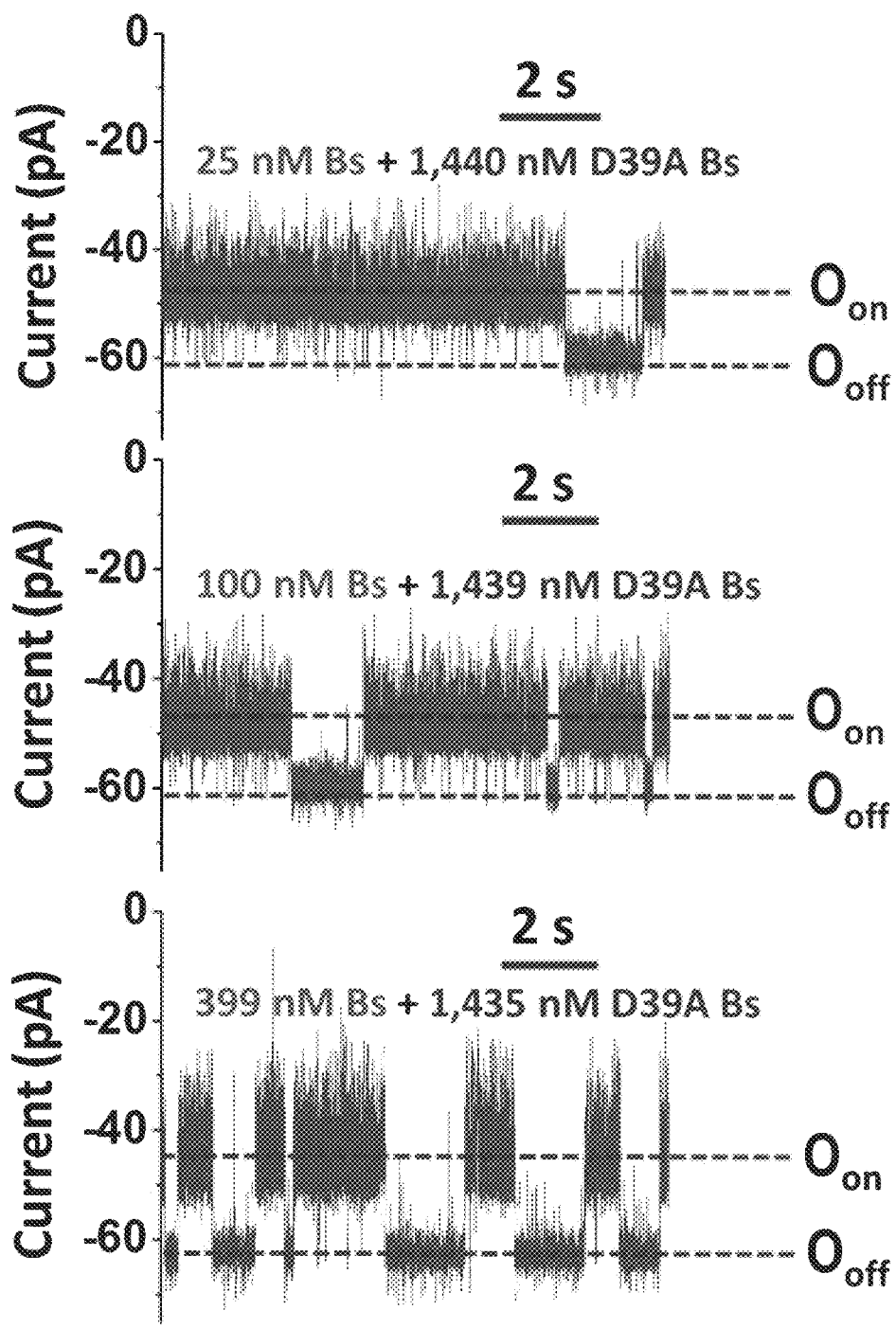
Figure 14B:
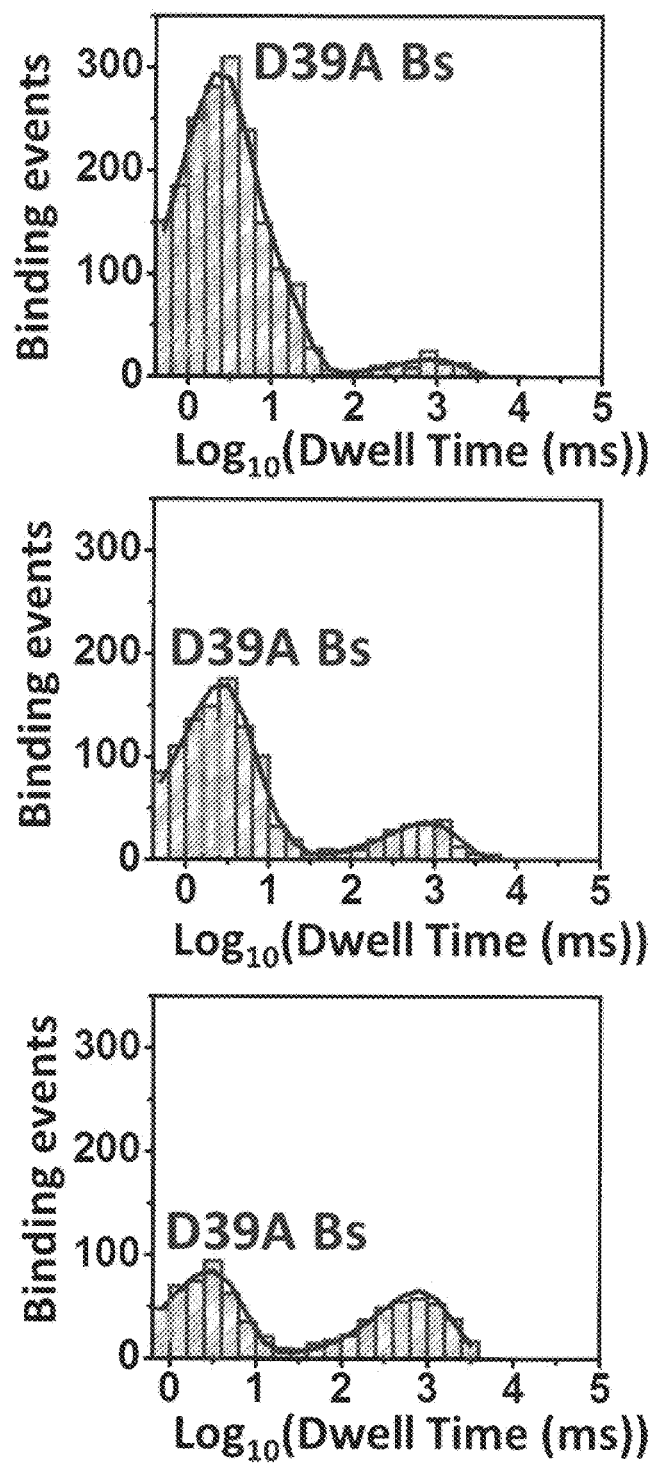

FIG. 14A is a series of representative single-channel current traces of OBn(GGS)$_2$ t-FhuA were collected at an applied transmembrane potential of −40 mV when different mixtures of protein ligands were added to the cis compartment: (i) 1,440 nM D39A Bs and 25 nM Bs (top trace); (ii) 1,439 nM D39A Bs and 100 nM Bs (middle trace); (iii) 1,435 nM D39A Bs and 399 nM Bs (bottom trace). The single-channel electrical traces were low-pass Bessel filtered at 1 kHz;

FIG. 14B is a series of representative event dwell-time histograms of the weak and strong PPI: (i) 1,440 nM D39A Bs and 25 nM Bs (top diagram); (ii) 1,439 nM D39A Bs and 100 nM Bs (middle diagram); (iii) 1,435 nM D39A Bs and 399 nM Bs (bottom diagram). The average $\tau_{off}$ dwell times, which corresponded to D39A Bs and Bs, respectively, were the following: (i) 4.1±0.1 ms and 904±1 ms (top diagram); (ii) 3.4±0.1 ms and 829±1 ms (middle diagram); (iii) 3.3±0.1 ms and 827±1 ms (bottom diagram).

Figure 15A:
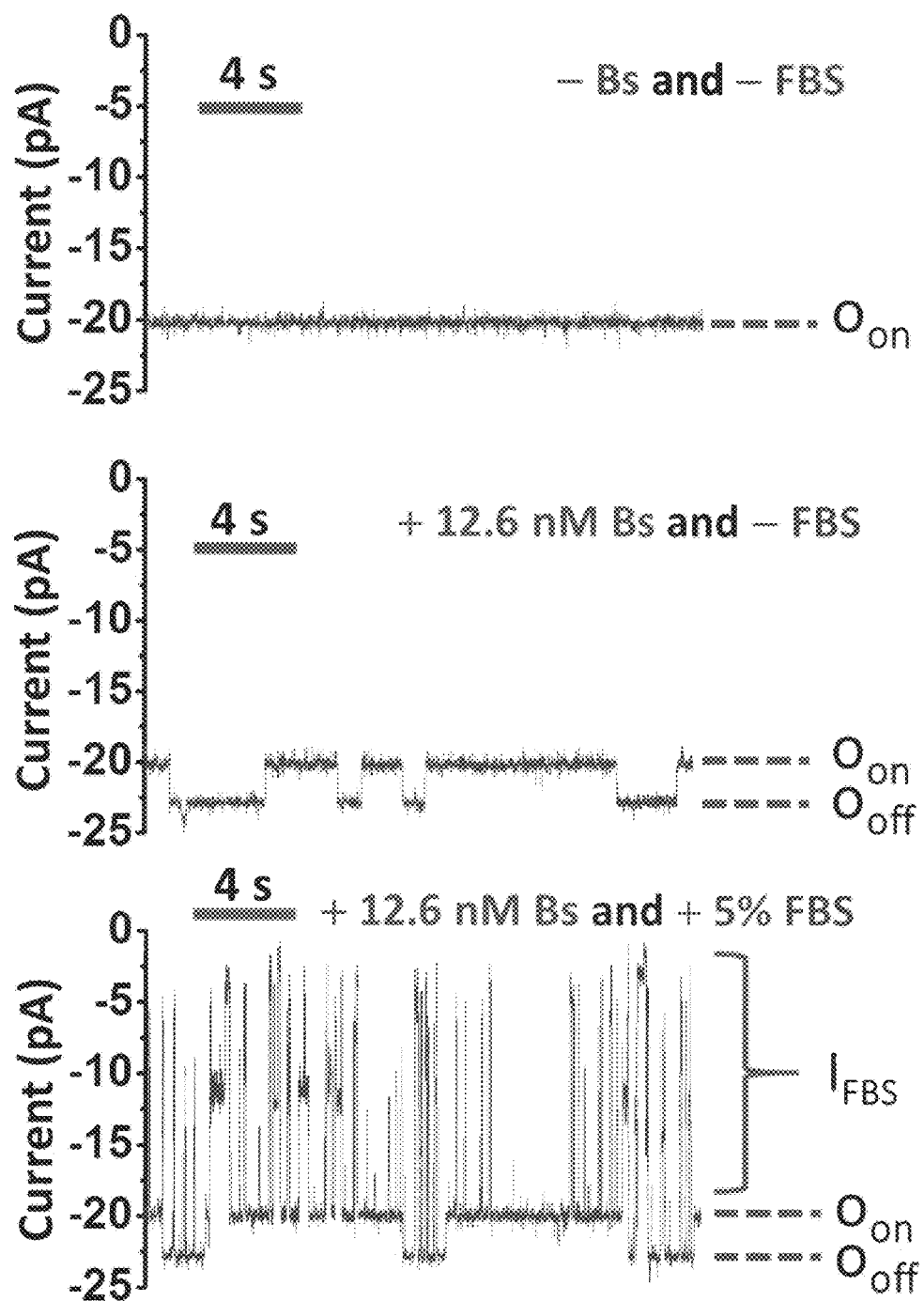
Figure 15B:
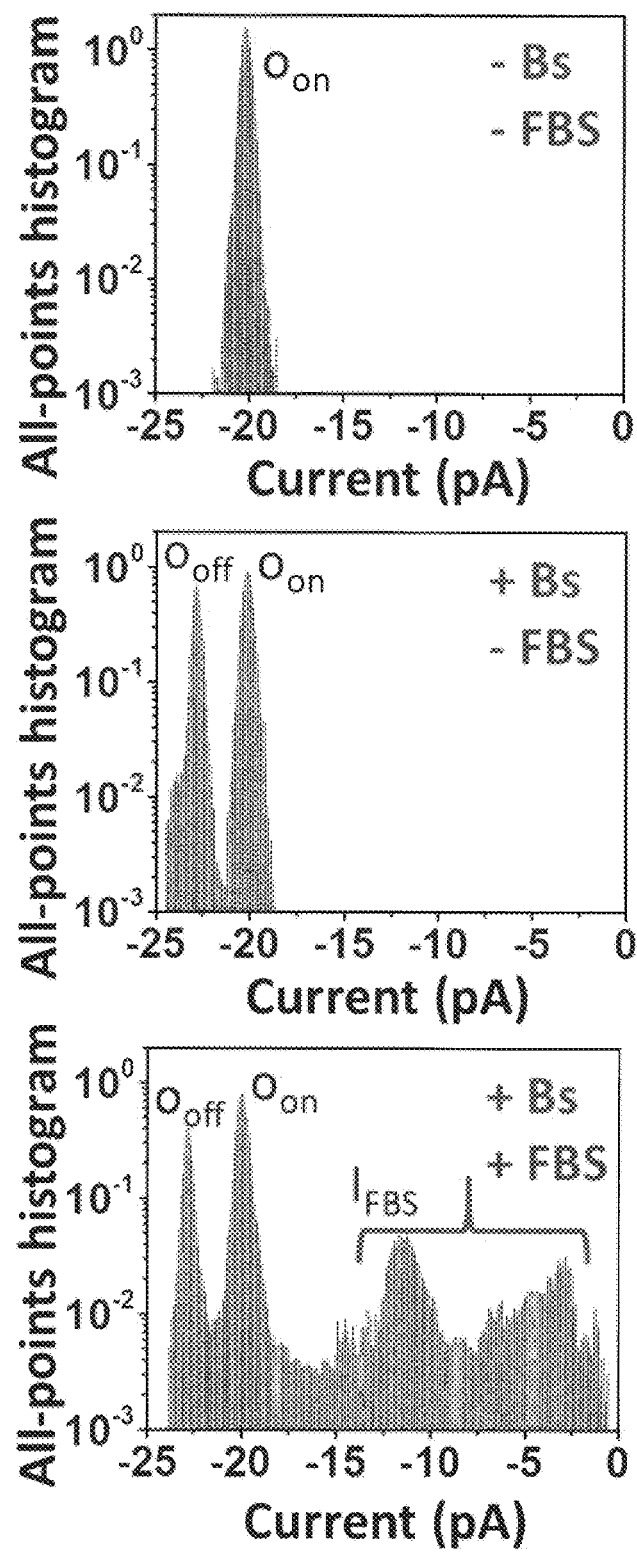
Figure 15C:
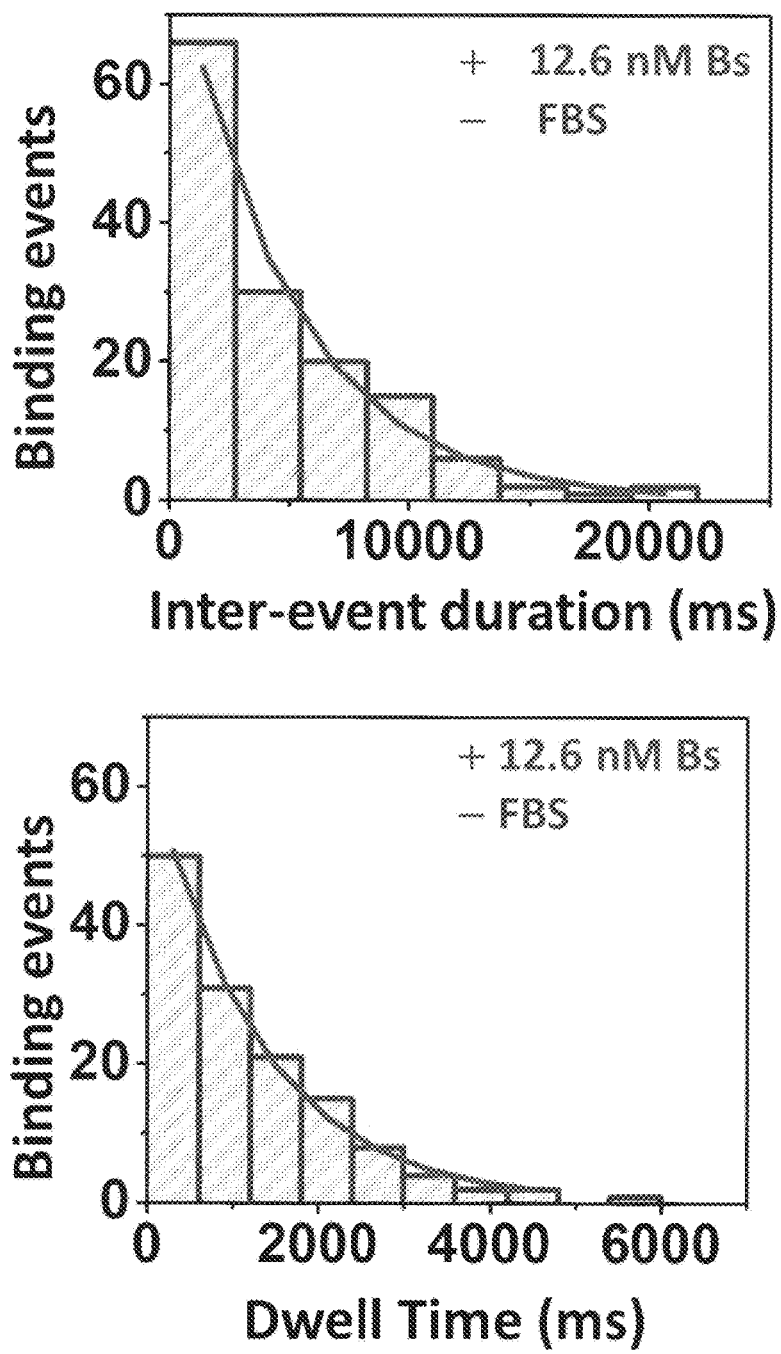
Figure 15D:
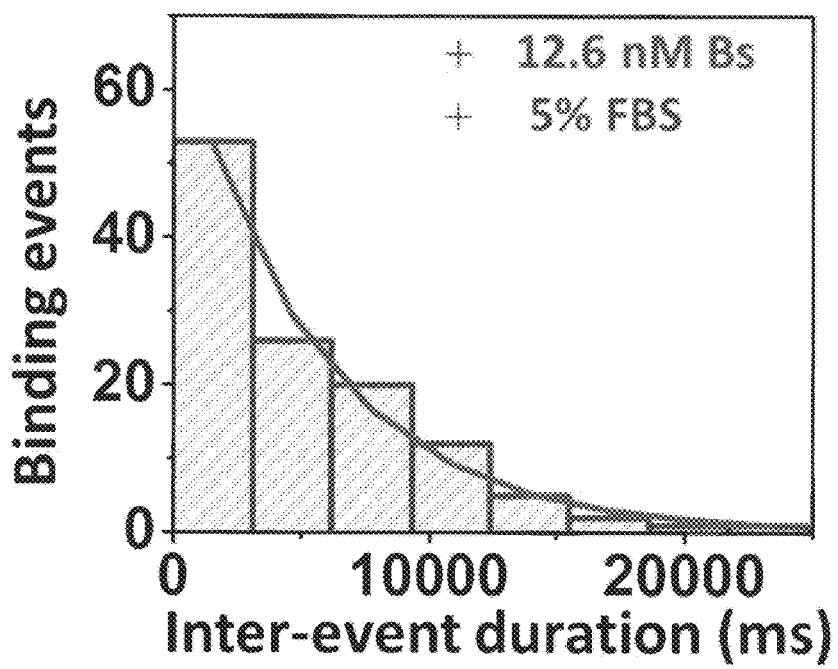
Figure 15D:
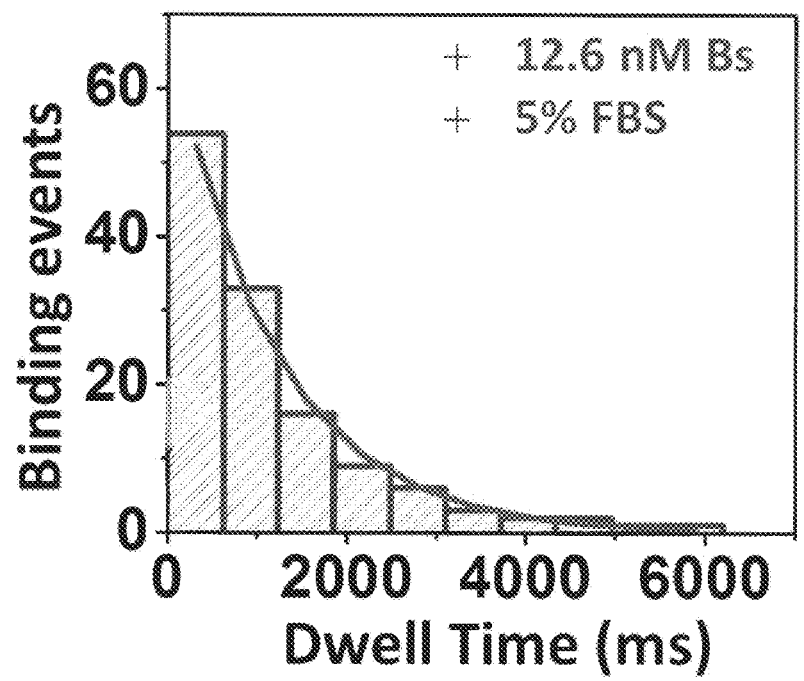
Figure 16:
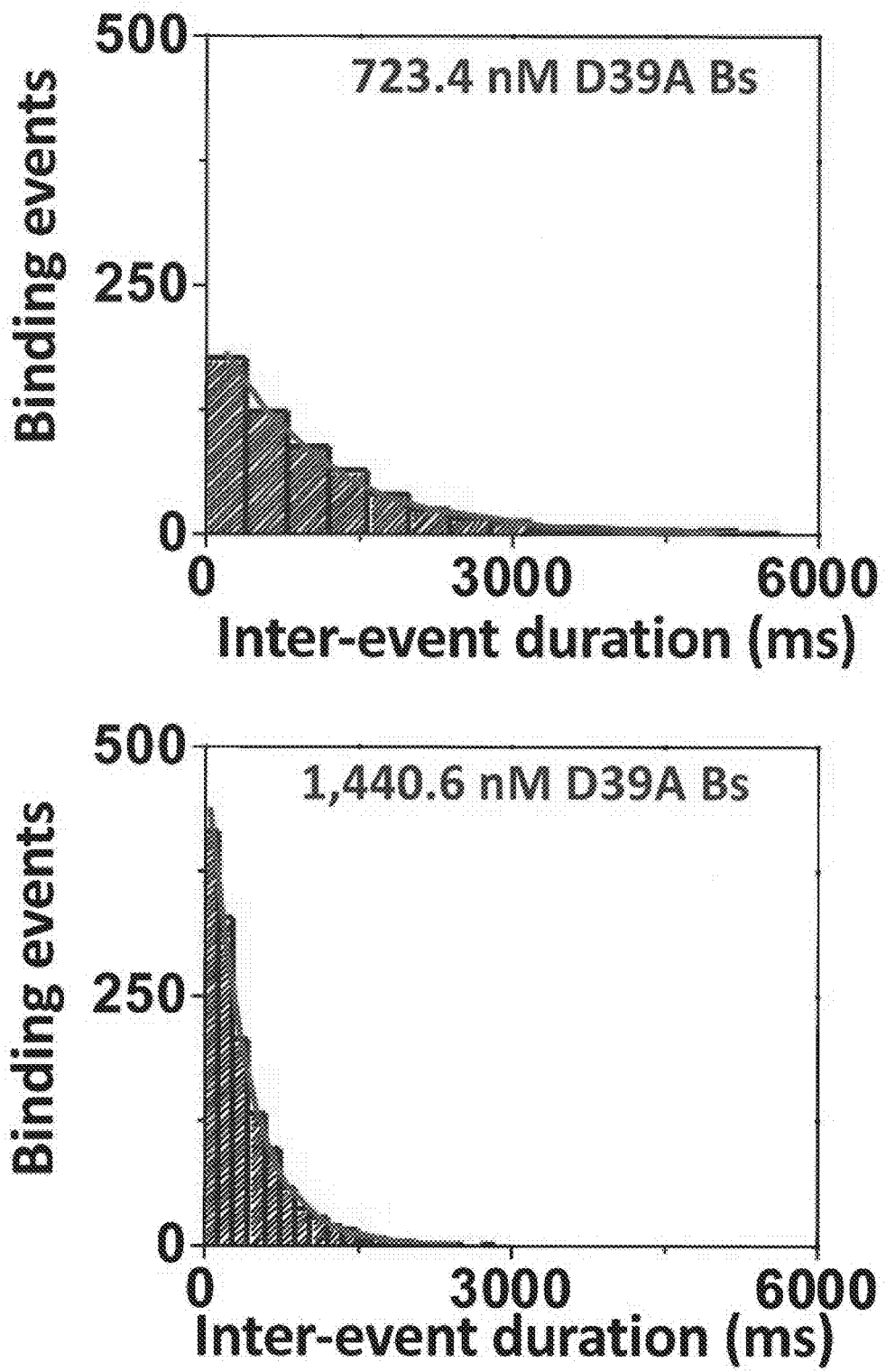

FIG. 15A is a series representative single-molecule binding events of the Bn-Bs pair using OBn(GGS)$_2$t-FhuA in 5% (v/v) FBS at an applied transmembrane potential of −15 mV and low-pass Bessel filtered at 40 Hz showing single-molecule protein detection and observation of transient PPI using a nanopore sensor in fetal bovine serum (FBS);

FIG. 15B is a series of representative normalized all-points histograms for the duration of the displayed single-channel traces in FIG. 15A;

FIG. 15C is a series of representative histograms of the inter-event durations ($\tau_{on}$) and the event dwell times ($\tau_{off}$) at 12.6 nM Bs and in the absence of FBS. The $\tau_{on}$ and $\tau_{off}$ duration determined from these fits were 5,182±200 ms and 1,272±53 ms, respectively;

FIG. 15D is a series of representative histograms of the inter-event durations ($\tau_{on}$) and the event dwell times ($\tau_{off}$) for the Bn-Bs interactions at 12.6 nM Bs and in the presence of 5% (v/v) FBS. The $\tau_{on}$ and $\tau_{off}$ durations determined from these histogram fits were 5,153±299 ms and 1,165±54 ms, respectively. An LLR test was used for the one-exponential fit of the histograms in C and D;

FIG. 16 is a series of representative histograms of the inter-event duration, $\tau_{on}$, of the PPI at two D39A Bs concentrations. The fits were accomplished using a logarithm likelihood ratio (LLR) test. For a confidence level C=0.95, it was determined that the best model was one-exponential fit. The $\tau_{on}$ values were ~855 and ~378 ms at D39 Bs concentrations of 723.4 nM and 1,440.6 nM, respectively.

Figure 17:
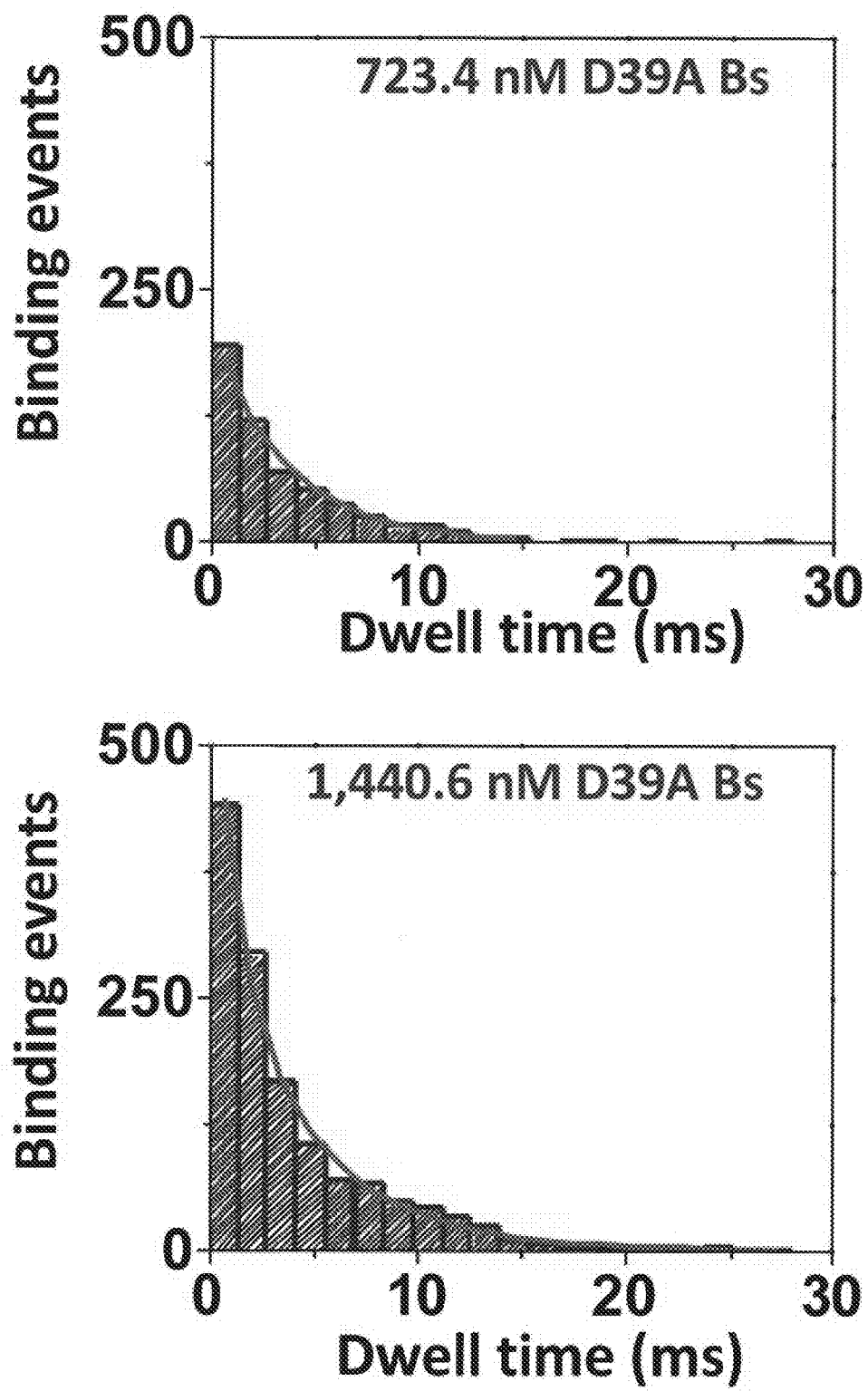

FIG. 17 is a series of representative event dwell-time histograms of the weak PPI at two D39A Bs concentrations. For a confidence level C=0.95, the best model was one-exponential fit. The $\tau_{off}$ values determined from these histograms were 3.6 ms at D39A Bs concentrations of 723.4 nM and 1,440.6 nM, respectively.

Figure 18:
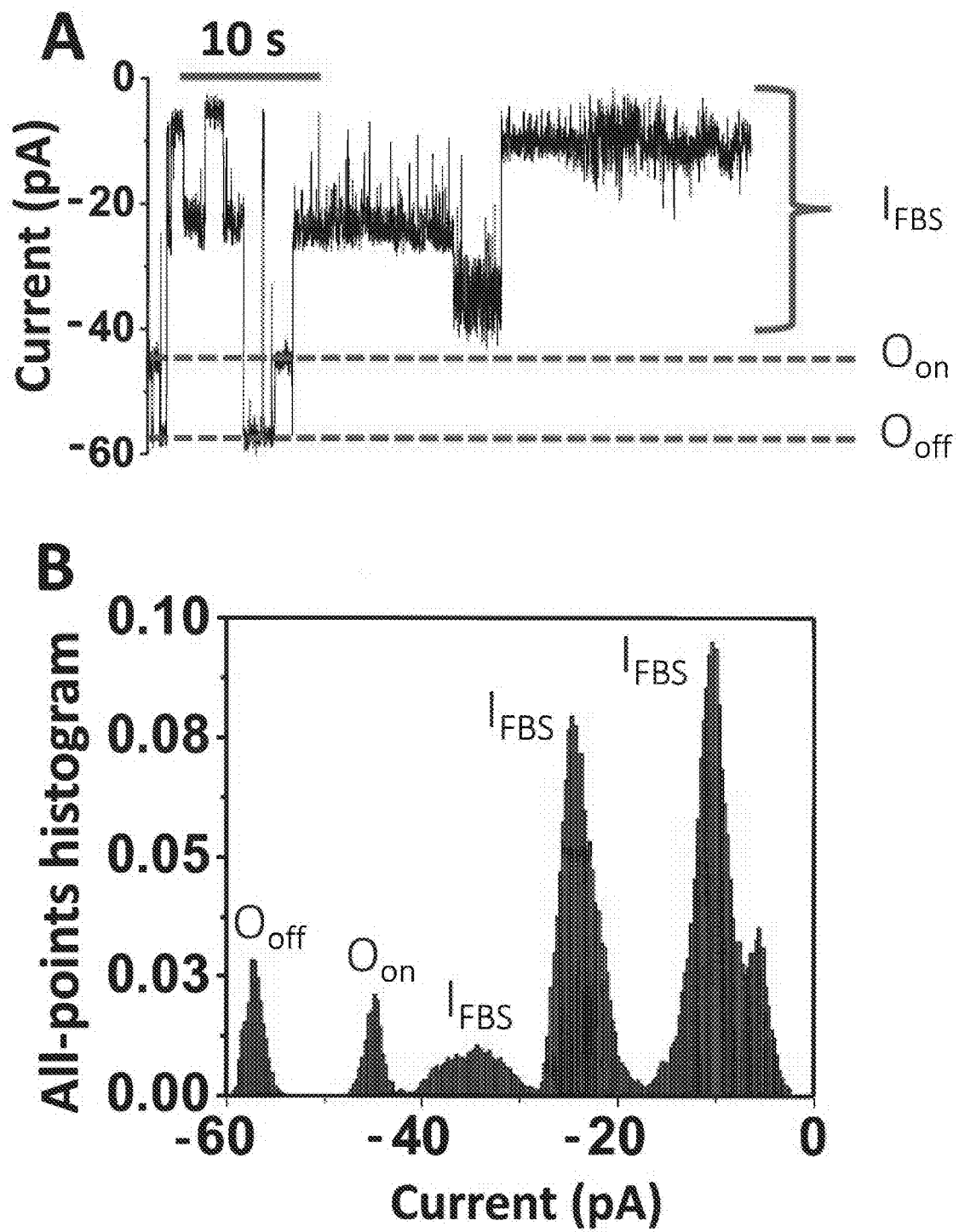

FIG. 18 is a graph (A) of a representative single-channel electrical recording of OBn(GGS)$_2$t-FhuA in the presence of 50.5 nM Bs and 1% FBS at an applied transmembrane potential of −40 mV; and a graph (B) of a normalized all-points current amplitude histogram for the trace displayed in (A). All recordings were performed in 300 mM KCl, 10 mM Tris·HCl pH 8, at a temperature of 23±1° C.

DETAILED DESCRIPTION OF THE INVENTION

Figure 1:
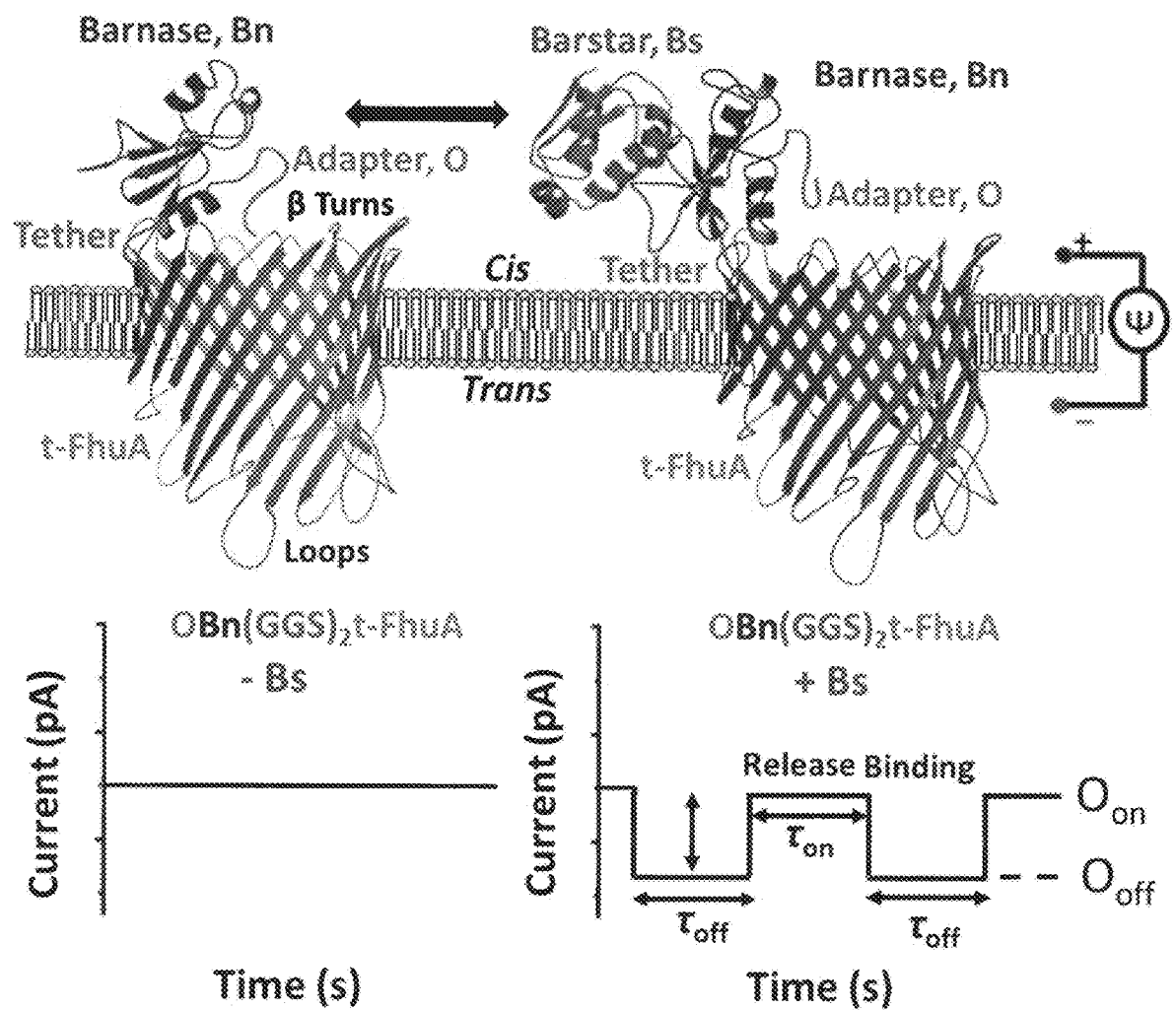
FIG. 1 is a schematic illustrating a single pore-based protein nanostructure for the detection of a single protein analyte (barstar, Bs) at the single-molecule level along with the mechanism of stochastic sensing of protein-protein interactions using high-resolution, single-channel electrical recordings of a single OBa(GGS)$_2$ t-FhuA protein nanopore at an applied transmembrane potential.

Referring to the figures, wherein like numeral refer to like parts throughout, there is seen in FIG. 1 a t-FhuA scaffold formed into a transmembrane pore according to the present invention. The present invention overcomes the challenges in the field by reconciling the unrestricted movements of the folded protein partners in solution with the transducing of their physical binding interactions into a specific and sensitive readout signal. More specifically, the present invention comprises a modular protein-pore based nanostructure formed from a monomeric β-barrel scaffold derived from ferric hydroxamate uptake component A (FhuA) of *E. coli*. This β-barrel domain, also called t-FhuA, is an extensive truncation of the wild-type FhuA protein, lacking large hydrophilic fragments, such as a 160-residue cork domain and five large extracellular loops (L3, L4, L5, L10, and L11). t-FhuA has both the N- and C-terminus on the periplasmic side of the protein. A protein receptor element was fused at the N-terminus of t-FhuA via a highly flexible (GGS)$_2$ linker. As a test case, the small 110-residue RNAse barnase (Bn) was used as a protein receptor to produce a fusion protein, simply named Bn(GGS)$_2$t-FhuA. The other interacting protein partner, here considered as a protein ligand, was the 89-residue barstar (Bs), an inhibitor of the Bn ribonuclease activity. The H102A mutant of Bn was used to abolish its ribonuclease activity, so that expression of this fusion protein would not pose toxicity to the host expression system. The membrane protein design of this fusion protein amalgamates the very hydrophobic t-FhuA barrel scaffold with the water-soluble folded domain of the Bn receptor. The single-polypeptide chain sensor opens up broad prospects for applications in nanoproteomics, specifically in the areas of protein detection, as well as in the development of novel approaches and tools for protein profiling and biomarker discovery.

More specifically, the t-FhuA scaffold has the sequence (SEQ. ID NO: 1)
LKEVQFKAGTDSLFQTGFDFSDSLDDDGVYSYRLTGLARSANAQQKGSEE

QRYAIAPAFTWRPDDKTNFTFLSYFQNEPETGNSEGSTYSRNEKMVGYSF

DHEFNDTFTVRQNLRFAENKTSQNSVYGNSEGSRKYVVDDEKLQNFSVDT

QLQSKFATGDIDHTLLTGVDFMRMRNDINAWFGYNSEGSSGPYRILNKQK

QTGVYVQDQAQWDKVLVTLGGRYDWADQESLNRVAGTTDKRDDKQFTWRG

GVNYLFDNGVTPYFSYSESFEPSSQVGKDGNIFAPSKGKQYEVGVKYVPE

DRPIVVTGAVYNLTKTNNLMADPEGSFFSVEGGEIRARGVEIEAKAALSA

SVNVVGSYTYTDAEYTTDTTYKGNTPAQVPKHMASLWADYTFFDGPLSGL

TLGTGGRYTNSEGSYTVVDALVRYDLARVGMAGSNVALHVNSEGSQVVAT

ATFRF.

The transmembrane pore provides a permeation pathway for ions as a result of the application of a voltage bias between the two sides of the membrane.

The use of a flexible peptide connector GGSGGS (SEQ. ID NO: 2), referred to as (GGS)$_2$, to attach an exemplary protein recognition element (protein receptor) MVINTFDGVADYLQTYHKLPDNYITKSEAQALGWVASKGNLADVAPGKSIGGDIFSNR EGKLPGKSGRTWREADINYTSGFRNSDRILYSSDWLIYKTTDAYQTFTKIR (SEQ. ID NO: 3) to form Bn(GGS)$_2$t-FhuA produces a uniform and quiet single-channel current, maintaining its signature for long periods. Under these contexts, the incubation of either half-side of the bilayer chamber with the binding protein ligand, Bs, failed to show reversible changes in the electrical signature of this protein pore-based nanostructure. This outcome suggested that even though the physical associations of the Bn and Bs proteins occurred in aqueous phase, these events were indistinguishable in the readout signal of our approach.

A further engineering of a short 12-residue polypeptide adaptor MGDRGPEFELGT (SEQ. ID NO: 4), referred to as O, at the N-terminus of Bn, and away from the binding site with Bs, produced a new protein pore-based nanostructure, OBa(GGS)$_2$t-FhuA, which featured an electrical signature that clearly distinguished from that noted with Bn(GGS)$_2$t-FhuA. Remarkably, the addition of the Bs protein ligand to the side of the protein addition, but not to the opposite side, determined the appearance of stochastic and reversible current transitions between two well-separated open substates of the OBa(GGS)$_2$t-FhuA protein, as seen in FIG. 1B, whose frequency and duration were dependent on the Bs concentration and strength of the Bn-Bs interactions, respectively. Therefore, t-FhuA served as a transducer of the transient PPI interactions that occurred in solution when the polypeptide adaptor, O, was engineered at the N-terminus of Bn. t-FhuA conveniently inserted into the membrane with a preferred orientation, which is a pivotal advantage in the functional features of this nanopore sensor.

The nanostructure of an exemplary embodiment of the present invention comprises a fusion protein with four functional domains, a transducer in the form of an ion permeation-based protein scaffold (an extensive truncation FhuA mutant; t-FhuA), a connector in the form of a flexible polypeptide linker (GGS)$_2$, a protein recognition element (barnase, Bn), as well as a peptide adaptor (charged polypeptide adaptor, O). The nanostructure thus has the sequence (SEQ. ID NO: 5)
MGDRGPEFELGTMVINTFDGVADYLQTYHKLPDNYITKSEAQALGWVASK

GNLADVAPGKSIGGDIFSNREGKLPGKSGRTWREADINYTSGFRNSDRIL

YSSDWLIYKTTDAYQTFTKIRGGSGGSLKEVQFKAGTDSLFQTGFDFSDS

LDDDGVYSYRLTGLARSANAQQKGSEEQRYAIAPAFTWRPDDKTNFTFLS

YFQNEPETGNSEGSTYSRNEKMVGYSFDHEFNDTFTVRQNLRFAENKTSQ

NSVYGNSEGSRKYVVDDEKLQNFSVDTQLQSKFATGDIDHTLLTGVDFMR

MRNDINAWFGYNSEGSSGPYRILNKQKQTGVYVQDQAQWDKVLVTLGGRY

-continued

DWADQESLNRVAGTTDKRDDKQFTWRGGVNYLFDNGVTPYFSYSESFEPS

SQVGKDGNIFAPSKGKQYEVGVKYVPEDRPIVVTGAVYNLTKTNNLMADP

EGSFFSVEGGEIRARGVEIEAKAALSASVNVVGSYTYTDAEYTTDTTYKG

NTPAQVPKHMASLWADYTFFDGPLSGLTLGTGGRYTNSEGSYTVVDALVR

YDLARVGMAGSNVALHVNSEGSQVVATATFRF.

It should be recognized that the particular sequence of the receptor is not a required element of the claimed invention. Instead, barnase was selected as an exemplary receptor because of its known relationship with barstar, thereby enabling the ability of the present invention to detect and measure protein-protein interactions to be evaluated against a known standard protein-protein relationship in the field. The present invention therefore contemplates the use of any desired receptor that has a corresponding target to be detected or evaluated for interactions with the receptor. For example, the present invention may include the use of any of the following receptors to detect protein-protein interactions with the corresponding receptor target protein, many of which are useful for studying, testing, evaluating, and designing treatments of cancers including leukemias: Ras-Raf interactions, proto-oncogene serine/threonine-protein kinase (Pim) interactions with Pim substrates and inhibitors, erine/threonine protein kinase CK2 kinase interactions with CK2 kinase substrates, and the mixed lineage leukemia (MLL) protein interactions with WDR5.

As discussed herein, the experiments also established that the present invention could detect at least two different protein-protein interactions at the same time. Thus, it is possible with the present invention to detect multiple proteins simultaneously by using sensors targeting each different protein in the same membrane.

The protein nanostructure maintains a stable open-conductance for long periods (the left side). When added to the cis side of the chamber at low nanomolar concentrations, the protein analyte produces a stochastic distribution of single-channel current transitions between well-define conductance sub-states $O_{on}$ and $O_{off}$ (the right side), the nature of which depends on both the strength of the Bn-Bs interactions as well as the effective concentration of Bs within the cis chamber. It should be noted that the transient Bn-Bs interactions in the form of reversible captures of Bs correspond to the $O_{off}$ level, which is a higher-conductance current state on the negative scale, because the voltage bias was negative. On the contrary, the releases of the Bs from Bn correspond to the $O_{on}$ level, which is a lower-conductance current state.

EXAMPLE

Design and Mutagenesis of the Expression Constructs

All the designed genes were constructed using conventional and assembly PCR techniques, and cloned into the expression vector pPR-IBA1 using respective restriction sites. Bn(ggs)$_2$t-fhua encoding barnase (Bn) at the N-terminus of the heavily truncated t-FhuA protein via a highly flexible Gly/Ser-rich linker and BsaI site was prepared using the Bn and t-fhua genes, as well as three PCR reactions. First PCR reaction was performed using Bn as a template DNA, the forward primer 5'-GAG CGG TCT CCA ATG GTT ATC AAC ACG TTT-3' (SEQ. ID NO: 6) and reverse primer 5'-CAG GCT GCC GCT GCC GCC TCT GAT TTT TGT AAA GGT-3' (SEQ. ID NO: 7). The second PCR reaction was performed using t-fhua as template DNA, and forward primer 5'-AGA GGC GGC AGC GGC GGC AGC CTG AAA GAA GTT CAG-3' (SEQ. ID NO: 8) and reverse primer 5'-CCG CGC GTA CCT TAA AAA CGA AAG GTT-3' (SEQ. ID NO: 9). The final PCR reaction was performed using PCR 1 and PCR 2 product as template DNA, and forward primer 5'-GAG CGG TCT CCA ATG GTT ATC AAC ACG TTT-3' (SEQ. ID NO: 6) and reverse primer 5'-CCG CGC GTA CCT TAA AAA CGA AAG GTT-3' (SEQ. ID NO: 9).

OBn[ggs]$_2$t-fhua, encoding the polypeptide adaptor, O, MGDRGPEFELGT (SEQ. ID NO: 4), fused at the N-terminus of Bn, Gly/Ser-rich linker, t-FhuA, as well as KpnI and BsaI sites at the 5' and 3' ends respectively, was prepared using Bn and t-fhua genes, as well as three PCR reactions. The first PCR reaction (conventional) was performed using Bn as a template DNA, along with the forward primer 5'-CAT GGT ACC ATG GTT ATC AAC ACG TTT GA-3' (SEQ. ID NO: 10) and reverse primer 5'-CAG GCT GCC GCT GCC GCC TCT GAT TTT TGT AAA GGT-3' (SEQ. ID NO: 7). For the second PCR reaction (conventional), t-fhua was used as a template DNA, along with the forward primer 5'-AGA GGC GGC AGC GGC GGC AGC CTG AAA GAA GTT CAG-3' (SEQ. ID NO: 8) and reverse primer 5'-CCG CGC GTA CCT TAA AAA CGA AAG GTT-3' (SEQ. ID NO: 9). The third PCR reaction (assembly) was performed using PCR 1's and PCR 2's products as template DNA, along with the forward primer 5'-CAT GGT ACC ATG GTT ATC AAC ACG TTT GA-3' (SEQ. ID NO: 10) and reverse primer 5'-CCG CGC GTA CCT TAA AAA CGA AAG GTT-3' (SEQ. ID NO: 9). The Bs gene encoded the barstar (Bs) protein analyte. All the purification tags were removed from the gifted plasmid (Courtesy Prof. Andreas Matouschek) using the forward primer 5'-ATC GGT CTC CAA TGA AAA AAG CA-3' (SEQ. ID NO: 11) and reverse primer 5'-AGC GGT CTC CGC GCT TTA AGA AAG TAT GAT GGT-3' (SEQ. ID NO: 12), then sub-cloned it into the pPR-IBA1 expression vector using BsaI restriction sites.

The Bs homologues used encompassed a double-alanine mutant (C40A/C82A), which was not expected to impact the binding interface with Bn, and has the sequence (SEQ. ID NO: 13)
MKKAVINGEQIRSISDLHQTLKKELALPEYYGENLDALWDALTGWVEYPL

VLEWRQFEQSKQLTENGAESVLQVFREAKAEGADITIILS.

Protein Expression and Purification

All the constructed genes were transformed into *Escherichia coli* BL21(DE3) cells for protein expression. Bn(GGS)$_2$t-FhuA and OBa(GGS)$_2$t-FhuA were expressed and purified as previously described. In the case of barstar (Bs), transformed cells were grown in Luria-Bertani medium at 37° C. until OD$_{600}$ reached a value of ~0.5, after which the temperature was changed to 20° C. Bs production was initiated by inducing the cell with IPTG when OD$_{600}$ was ~0.7. After induction, the cells were further cultured for an additional period of ~18 hours at 20° C. After the protein expression period, the cells were collected by centrifugation at 3,700×g for 30 min at 4° C., then resuspended in 150 mM KCl, 50 mM Tris.HCl, 5 mM EDTA, pH 8. The cell lysis was accomplished using a Model 110L microfluidizer (Microfluidics, Newton, Mass.). Cell lysates were centrifuged at 108,500×g for 30 min at 4° C. to separate the insoluble pellet and supernatant. The supernatant was further processed for ammonium sulfate precipitation. In the first step, ammonium sulfate was slowly dissolved in supernatant to a final concentration of 10% (w/v) at 4° C. for 30 min. Later, the supernatant was centrifuged at 108,500×g for 30 min at 4° C. to separate the precipitate and supernatant. Further, the supernatant was processed like the previous step with 40% ammonium sulfate. The collected supernatant was dialyzed extensively against 20 mM Tris.HCl, pH 8, overnight at 4° C. Dialyzed supernatant was then purified on the Q-Sepharose column (Bio-Rad, Hercules, Calif.) using a linear salt gradient of 0-1 M KCl, 20 mM Tris.HCl, pH 8. Pure fractions were further passed through the Superdex-75 size-exclusion (SEC) column (GE Healthcare Life Sciences, Pittsburg, Pa.) as a refining purification step. Pure barstar was then further stored in freezer at −80° C. All proteins were judged to be greater than 95% in purity by the SDS-PAGE.

Protein Refolding

Lyophilized $Bn(GGS)_2$t-FhuA and $OBa(GGS)_2$t-FhuA were solubilized in 200 mM KCl, 8 M urea, 50 mM Tris.HCl, pH 8 to a final concentration of 30-50 µM, and incubated at room temperature for at least 4 hours before refolding. Later, n-dodecyl-β-D-maltopyranoside (DDM) was added to both denatured samples to a final concertation of 1.5% (w/v) and were immediately dialyzed against the buffer containing 200 mM KCl, 20 mM Tris.HCl, pH 8, at 4° C. for a duration of at least 72 h. Then, the refolded protein samples were passed through the Superdex 200 HR SEC column equilibrated with 200 mM KCl, 20 mM Tris.HCl, pH 8, 0.5% DDM, using the BioLogic DuoFlow Chromatography System (Bio-Rad). Protein concentrations were determined by their molar absorptivity at a wavelength of 280 nm.

Single-Channel Electrical Recordings using Planar Lipid Bilayers

Single-channel electrical recordings were executed at room temperature employing synthetic planar lipid bilayers, which contained 1,2 diphytanoyl-sn-glycero-phosphocholine (Avanti Polar Lipids, Alabaster, Ala.). The planar lipid bilayer was formed across an 80 µm-diameter aperture within a 25 µm-thick Teflon film (Goodfellow Corporation, Malvern, Pa.). This aperture was pretreated with hexadecane (Sigma-Aldrich, St. Louis, Mo.) dissolved in highly purified pentane (Fisher HPLC grade, Fair Lawn, N.J.) at a concentration of 10% (v/v). The refolded pore-forming proteins were added to the cis compartment, which was at ground, to a final concentration in a range between 0.3 and 1 ng/µl. The single-channel electrical currents were acquired using an Axopatch 200B patch-clamp amplifier (Axon Instruments, Foster City, Calif.). For all experiments, the electrolyte solution contained 300 mM KCl, 10 mM Tris-HCl, pH 8. The single-channel electrical currents were low-pass filtered with an 8-pole Bessel filter (Model 900, Frequency Devices, Ottawa, Ill.) at a frequency of 10 kHz and sampled at 50 kHz, unless otherwise stated. The analog electrical signals were digitized using a DigiData 1440 A A/D converter (Axon), which was connected to a PC desktop (Dell Corporation, Austin, Tex.). For both data acquisition and analysis, a pClamp 10.5 software package (Axon) was used. In the case of the binding Bn-Bs experiments, the cis compartment was washed out using freshly prepared buffer to remove the remaining nanopore proteins from the chamber, namely $Bn(GGS)_2$t-FhuA or $OBa(GGS)_2$t-FhuA.

Design, Creation, and Single-molecule Analysis of the $Bn(GGS)_2$t-FhuA Protein

Figure 6:
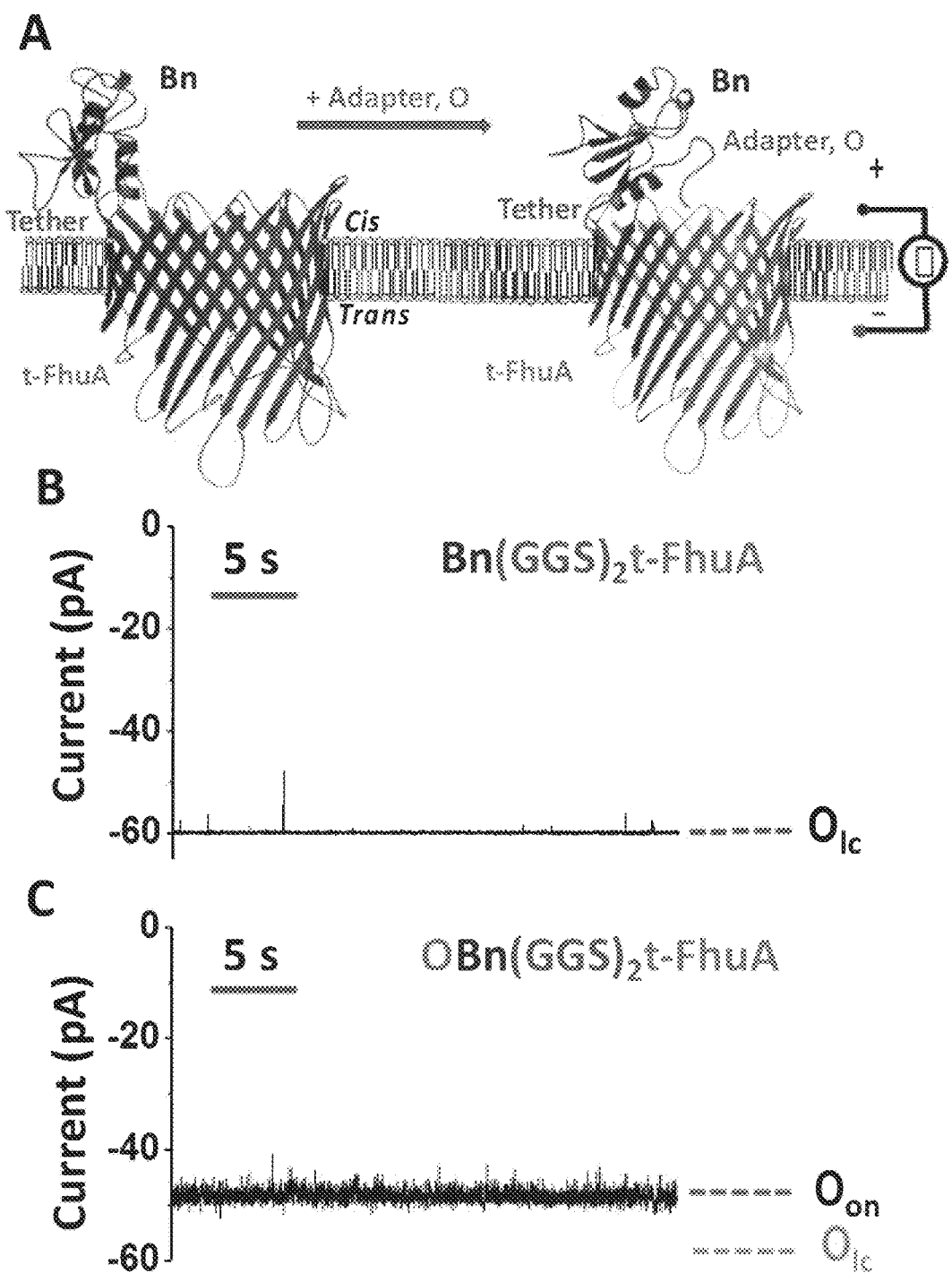
FIG. 6 is a schematic of the engineering of a flexible and negatively charged polypeptide adaptor, O, at the N terminus of the protein sensing element, Bn.

The engineering of this pore-based nanostructure relied on an unusually robust barrel scaffold derived from FhuA. This protein scaffold, here named t-FhuA, represents an extensive truncation of the native FhuA, a 455-residue polypeptide, which resulted from the extensive deletions of five major extracellular loops, L3, L4, L5, L10, and L11, as well as, the inner, N-terminal, 160-residue cork domain of native FhuA. This represents ~64% of the initial length of the wild-type FhuA protein. This sensor was designed and developed as a modular single-polypeptide chain protein overcoming the need for chemical modification via covalent attachment of other functional domains. A very flexible linker $(GGS)_2$ was fused at the N-terminus of t-FhuA, mediating the connection of the recognition event transducer, t-FhuA, with the protein recognition element, barnase (Bn), a 110-residue polypeptide, thus making $Bn(GGS)_2$t-FhuA, a protein pore-based nanostructure. It was critically important that the fusion of Bn to the N-terminus of $(GGS)_2$t-FhuA would not produce substantial population of current fluctuations resulted by the movements of $(GGS)_2$, Bn, or both, around the periplasmic opening of the pore. Indeed, we examined two protein pore-based nanostructures, encompassing a $(GGS)_2$ flexible linker fused to either N-terminus or C-terminus of t-FhuA, which are only ~0.7 nm apart from each other. Such protein pore-based nanostructures produced a closely similar unitary conductance with an average of 1.5±0.1 nS (n=5) or 1.6±0.1 nS (n=24), respectively, at a transmembrane potential of −40 mV and in 300 mM KCl, 10 mM Tris-HCl, pH 8. In both cases, the single-channel electrical traces exhibited stability of the open-state current and no significant current fluctuations for long periods. One example of such a relatively quiet single-channel electrical signature is illustrated in FIG. 6. When $Bn(GGS)_2$t-FhuA was added to the cis side of the chamber, whose fusion site was at the N-terminus of t-FhuA, a uniform single-channel current with a unitary conductance of 1.5±0.1 nS (n=5) was noted. In FIG. 6, the top panel shows the schematic cartoons of the nanostructure $Bn[GGS]_2$t-FhuA with and without the polypeptide adaptor, O. The second panel shows the single-channel electrical trace acquired with $Bn[GGS]_2$t-FhuA at a transmembrane potential of −40 mV. The current amplitude corresponds to a large-conductance open state $O_{1c}$. The third panel shows the single-channel electrical trace acquired with $OBn[GGS]_2$t-FhuA at a transmembrane potential of −40 mV. It should be noted that the current amplitude corresponds to that of the $O_{on}$ open state measured in FIG. 2 and $I_{1c} > I_{on}$. Electrical traces were low-pass Bessel filtered at a frequency of 100 Hz.

Design, Creation, and Single-Molecule Analysis of $OBa(GGS)_2$t-FhuA

An additional 12-residue polypeptide adaptor, O, was fused at the N-terminus of Bn, resulting in $OBa(GGS)_2$t-FhuA, a new pore-based nanostructure. It was anticipated that this prolongation with an O polypeptide would transiently occlude the ionic flux across the pore lumen of t-FhuA, resulting in fast flickering current fluctuations. In excellent agreement with expectation, single-channel electrical traces acquired with $OBa(GGS)_2$t-FhuA showed a highly frequent population of brief current blockades with a frequency, duration, and inter-event interval of 1078±815 $s^{-1}$, 30±14 µs, 1.0±0.4 ms (n=7) (FIG. 8, FIG. 9). However, the most important finding of these measurements was the fact that the unitary conductance of $OBa(GGS)_2$t-FhuA decreased to 1.23±0.03 nS (n=8), on the average by ~16.3%, which corresponded to a unitary current of −49.27±1.28 pA (n=8) for $OBa(GGS)_2$t-FhuA as compared to −58.81±3.94 pA for $Bn(GGS)_2$t-FhuA at a transmembrane potential of −40 mV (FIGS. 6B and C). It is likely that, by fusing the polypeptide adaptor, O, to the N-terminus of Bn(GGS)$_2$t-FhuA, Bn fluctuated closer to the periplasmic pore opening of t-FhuA, thus reducing the ionic flux, so the unitary conductance.

Figure 2:
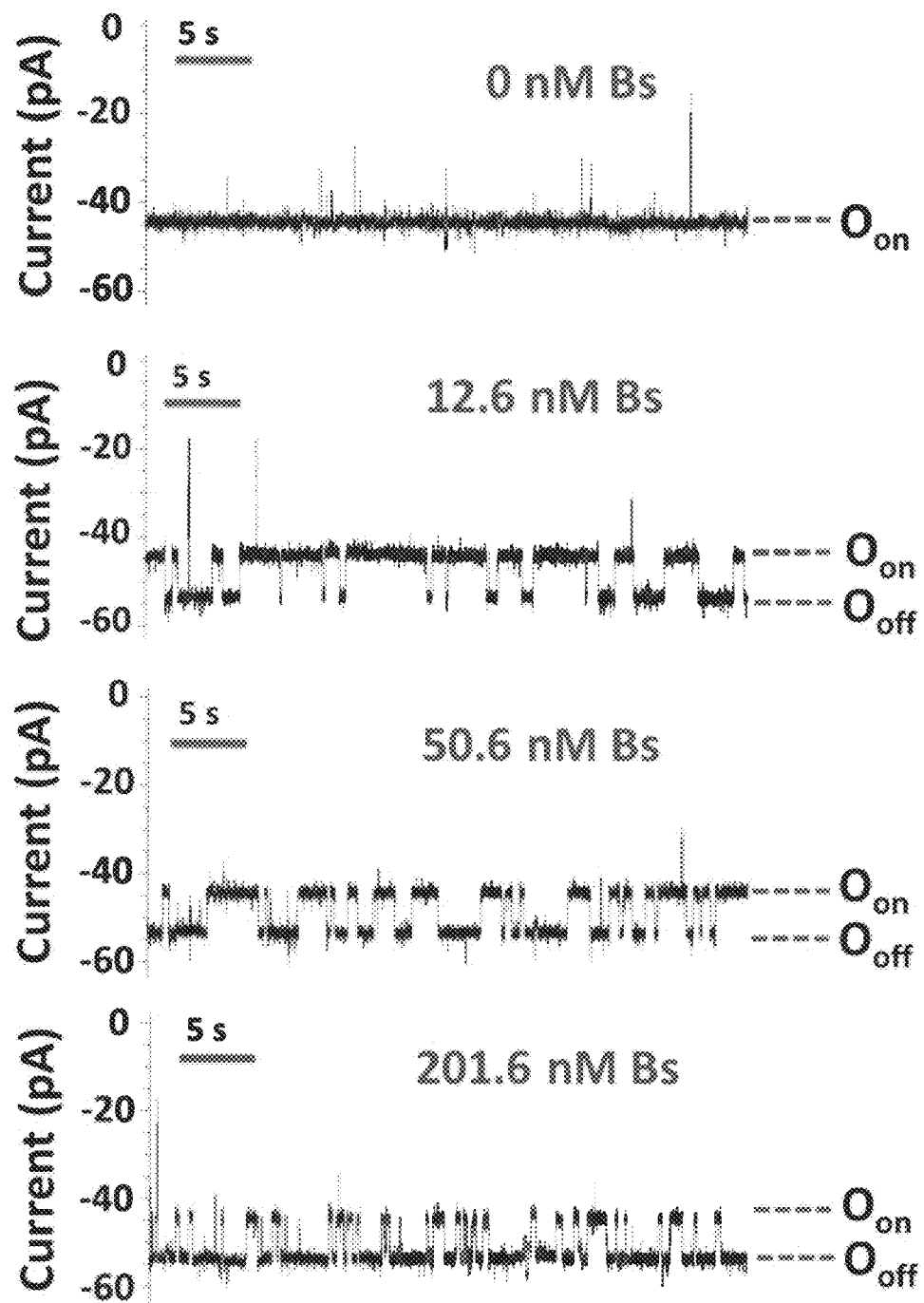
FIG. 2 is a series of single-molecule captures of transient PPI between Bn and Bs using an engineered OBn[GGS]$_2$t-FhuA protein nanopore in the absence and presence of Bs at the following concentrations: (top) 0 nM Bs; (second) 12.63 nM Bs; (third) 50.58 nM Bs; (bottom) 201.60 nM.

Real-Time Sampling of the Transient Bn-Bs Interactions in Aqueous Phase at Single-Molecule Resolution Remarkably, when barstar (Bs), an 89-residue inhibitor of Bn and used here as a protein ligand, was added to the cis chamber at low nanomolar concentrations, we were able to detect reversible current transitions between O$_{on}$, a noisier, lower-current amplitude open-state level, and O$_{off}$, a quieter, higher-current amplitude open-state level (FIG. 2). Reversible captures of Bs by an engineered Bn, as part of the biosensing nanostructure, was observed by current transitions that were stochastic in duration, but uniform in current amplitude. The Bs protein analyte was added to the cis side of the chamber. O$_{on}$ represents the Bs-released or Bs-unbound state, which is also noted in the absence of Bs, whereas O$_{off}$ represents the Bs-bound state. The addition of 12.6 nM Bs produced current transitions, whose frequency and dwell time were ~0.2 s$^{-1}$ and 1.1±0.1 s (n=3), respectively, at a transmembrane potential of ~40 mV as seen in Table 1 below:

TABLE 1

The average values of the $\tau_{on}$ an $\tau_{off}$ time constants as well as the k$_{on}$ and k$_{off}$ kinetic rate constants for the transient Bn-Bs interactions.

| [Bs] (nM) | $\tau_{on}$ (ms) | $\tau_{off}$ (ms) | k$_{on}$ (M$^{-1}$s$^{-1}$) × 10$^{-7}$ | k$_{off}$ (s$^{-1}$) |
|---|---|---|---|---|
| 12.6 | 5,054 ± 2,707 | 1,111 ± 46 | 1.57 ± 0.84 | 0.90 ± 0.04 |
| 25.3 | 2,040 ± 997 | 1,126 ± 62 | 1.94 ± 0.95 | 0.89 ± 0.05 |
| 50.5 | 1,595 ± 480 | 1,197 ± 36 | 1.24 ± 0.37 | 0.84 ± 0.03 |
| 100.9 | 920 ± 190 | 1,263 ± 146 | 1.08 ± 0.22 | 0.80 ± 0.10 |
| 201.6 | 595 ± 300 | 1,254 ± 147 | 0.83 ± 0.42 | 0.81 ± 0.10 |
| 402.3 | 177 ± 50 | 1,166 ± 81 | 1.41 ± 0.39 | 0.86 ± 0.06 |
| 627.2 | 117 ± 6 | 1,109 ± 173 | 1.37 ± 0.65 | 0.92 ± 0.16 |

All single-channel electrical traces were low-pass 8-pole Bessel filtered at 10 kHz and sampled at a frequency of 50 kHz. The applied transmembrane potential was −40 mV. For further data analysis and figure presentation, the single-channel electrical traces were further low-pass 8-pole Bessel filtered at 100 Hz. All recordings were performed in 300 mM KCl, 10 mM Tris.HCl, pH 8, at a temperature of 23±2° C.

These reversible current transitions were interpreted as reversible capture and release events of Bs by Bn. Thus, the transduction mechanism of the PPIs was mediated through the direct reversible changes in both the amplitude of the single-channel electrical current as well as the amplitude of the flickering noise fluctuations, more than likely induced by the O connector. Moreover, the fact that these current transitions were observed only on Bs was added to the cis side, but not to the trans side of the chamber confirmed our previous finding that truncation FhuA protein pore mutants inserted into a planar lipid bilayer with a preferred orientation) in such a way that the extracellular loops face the trans side and periplasmic β turns face the cis side (the protein addition side). As discussed above, in the absence of Bs within the cis side, we noted O$_{on}$, a noisy and lower-conductance current level of OBa(GGS)$_2$t-FhuA (FIG. 2A; FIG. 6C, FIG. 8). Interestingly, when 12.63 nM Bs was added to the cis chamber, reversible transitions to a quieter and higher-conductance level, O$_{off}$, were noted, whose frequency and dwell time were 0.2±0.1 s$^{-1}$ and 1111±46 ms (n=3), respectively. It was interpreted that the higher-conductance and reversible "off" events represent stochastic binding Bn-Bs interactions, pulling away Bn from the pore opening, so that increasing the open-state current to a level closely similar to that noted with Bn(GGS)$_2$t-FhuA alone (FIG. 6B). This change in Bn positioning with respect to the periplasmic opening of the pore moved the O polypeptide adaptor further away, which explains a quieter and higher-conductance open state, O$_{off}$. The current amplitudes of the O$_{on}$ and O$_{off}$ levels permitted a clear separation of the "off" (binding) and "on" (unbinding or release) events, showing a difference of 10.2±2.1 pA (n=3) at a transmembrane potential of −40 mV. This finding enabled an easy dwell time analysis with low-pass Bessel filterings up to 100 Hz (FIG. 2).

The current amplitudes of the O$_{off}$ and O$_{on}$ levels permit an unambiguous separation of the "off" (quiet open substate) and "on" (noisy open substate) events, showing a difference of 10±2 pA (n=3). Thus, the transducing mechanism of the PPI was mediated through the direct reversible changes in both the open-state conductance as well as the flickering noise fluctuations. Notably, these reversible current transitions were observed only when Bs was added to the cis side, but not to the trans side (compare FIG. 11 with FIG. 12). The panels in FIG. 13 indicate no change in the single-channel electrical signature after the addition of Bs to the trans side. This result confirmed the insertion of the OBn(GGS)$_2$t-FhuA nanopore into the lipid bilayer with a preferred orientation. The single-channel traces were low-pass Bessel filtered at a frequency of 100 kHz. All recordings were performed under an applied potential of −40 mV and in 300 mM KCl, 10 mM Tris.HCl, pH 8. The traces were collected at a temperature of 23±1° C. This finding confirmed that the truncation FhuA protein pore mutants insert into a planar lipid bilayer with a preferred orientation. Thus, these insertions occurred in such a way that the loops faced the trans side and the $_R$ turns faced the cis side as seen in FIG. 1A.

Single-Molecule Kinetic Details of the Transient Bn-Bs Interactions

Figure 3:
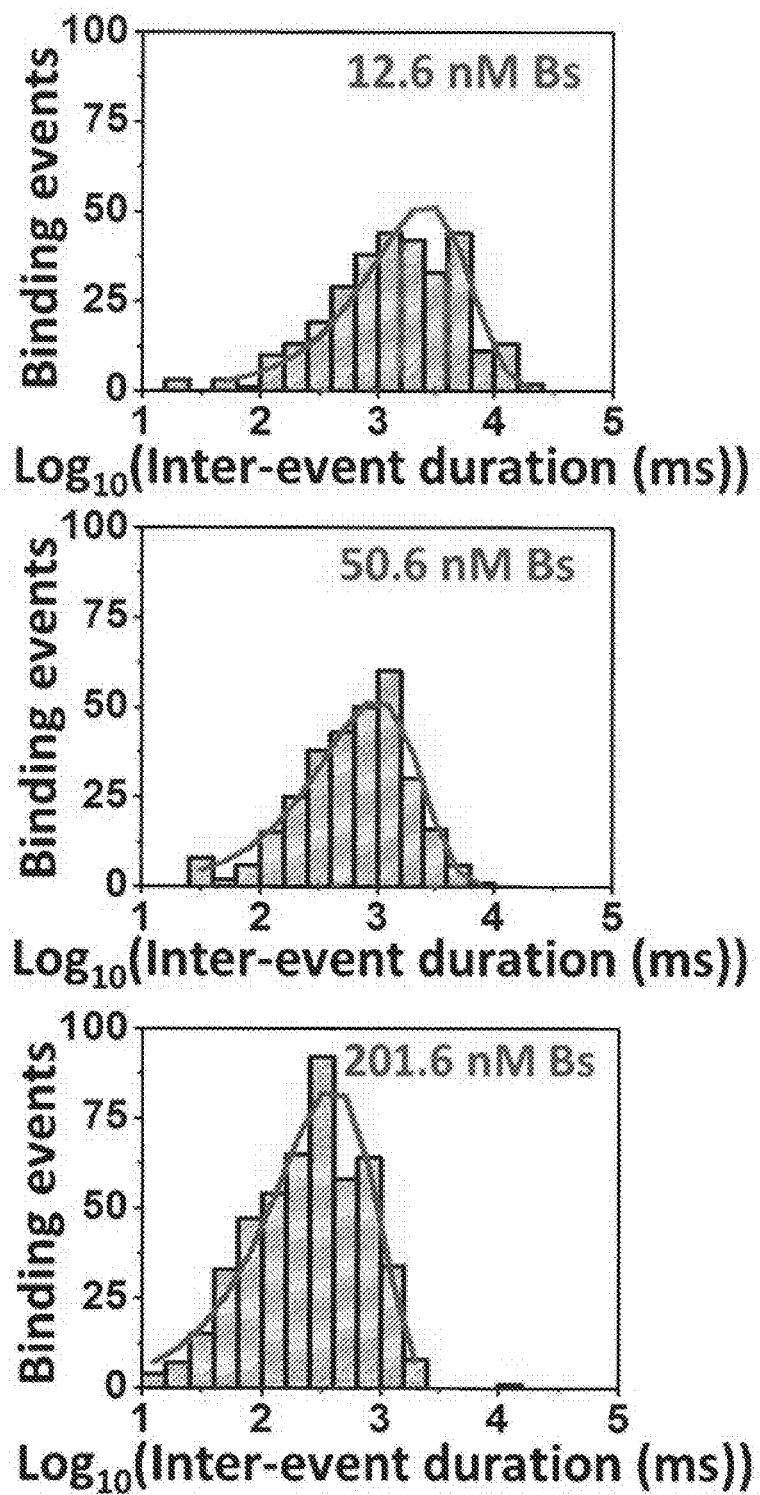
FIG. 3 is a series of representative histograms of inter-event duration ($\tau_{on}$) of the binding Bn-Bs interactions at the various following concentrations of the protein analyte: (top) 12.63 nM Bs; (middle) 50.58 nM Bs; (bottom) 201.60 nM Bs.
Figure 4:
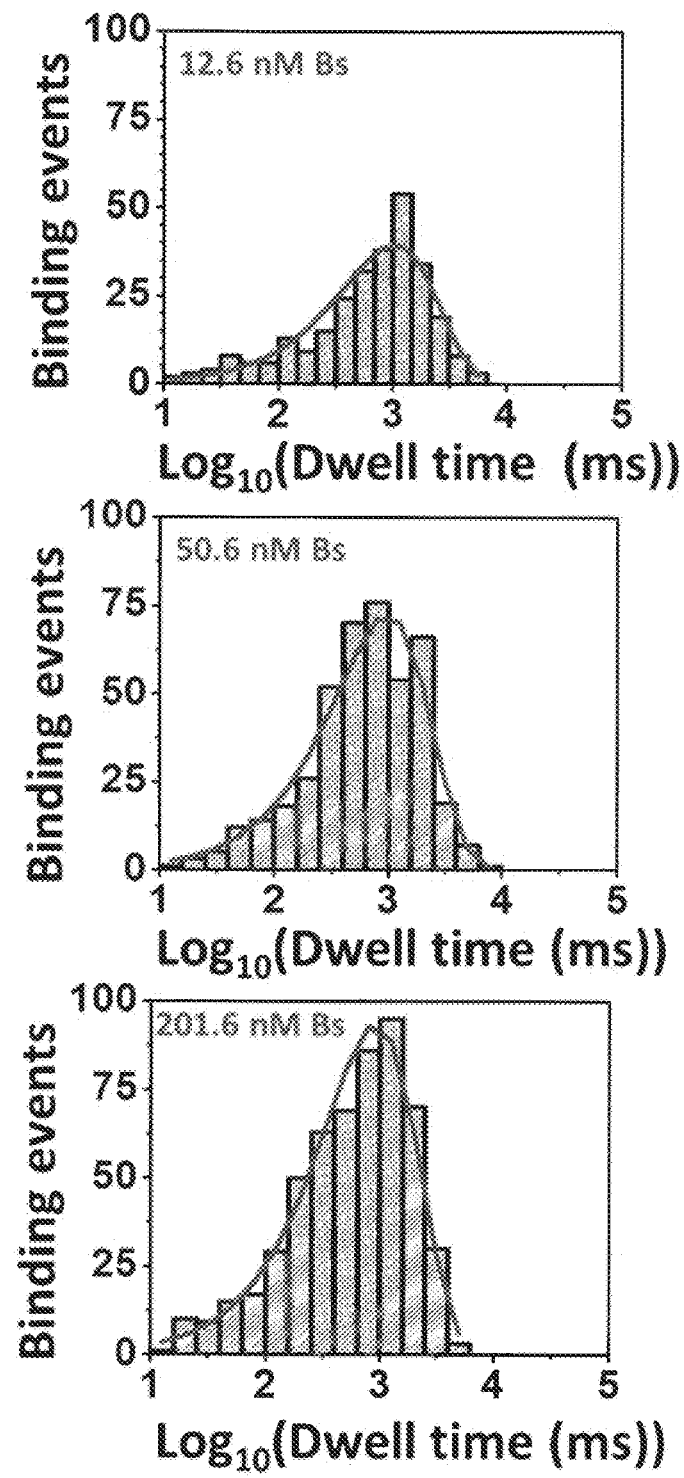
FIG. 4 is a series of representative dwell-time histogram of the $\tau_{off}$ time constant of the binding Bn-Bs interactions at various Bs concentrations: (top) 12.63 nM Bs; (middle) 50.58 nM Bs; (bottom) 201.60 nM Bs.

For a better understanding of the single-molecule kinetic details of the binding Bn-Bs interactions, the Bs protein analyte was gradually increased within the cis chamber. As expected, the frequency of the binding Bn-Bs interactions increased by increasing the Bs concentration. This finding was visually noted with 50.58 and 201.60 nM Bs within the cis side of the chamber, as illustrated in FIG. 2C and FIG. 2D, respectively. Individual standard dwell-time analysis of the "on" (release) and "off" (binding) events is shown in FIG. 3 and FIG. 4, respectively. In FIG. 4, the fitting method featured a variable metric on the logarithm of the exponential probability function. At a confidence level C=0.95, the best model was one-exponential fit, because $\chi_{crit}$=5.99 and $\chi_{1\to2}<\chi_{crit}$. Fits to two-exponential time distributions were statistically worse than the one-exponential fit, as indicated by the values of $\chi_{1\to2}$, which were 3.83 (A), −0.00118 (B), and −0.121 (C). The $\tau_{off}$ dwell times determined from these histograms were 1038±1 ms at 12.63 nM, 939.01±1 ms at 50.58 nM, and 920±1 ms at 201.60 nM. For the data analysis, all the single-channel electrical traces were filtered with a low-pass, 8-pole Bessel filter at a frequency of 500 Hz. Single-channel transitions analyzed for these histograms were collected from individual single-channel electrical traces, whose durations were within a range of 15-20 min.

Figure 5:
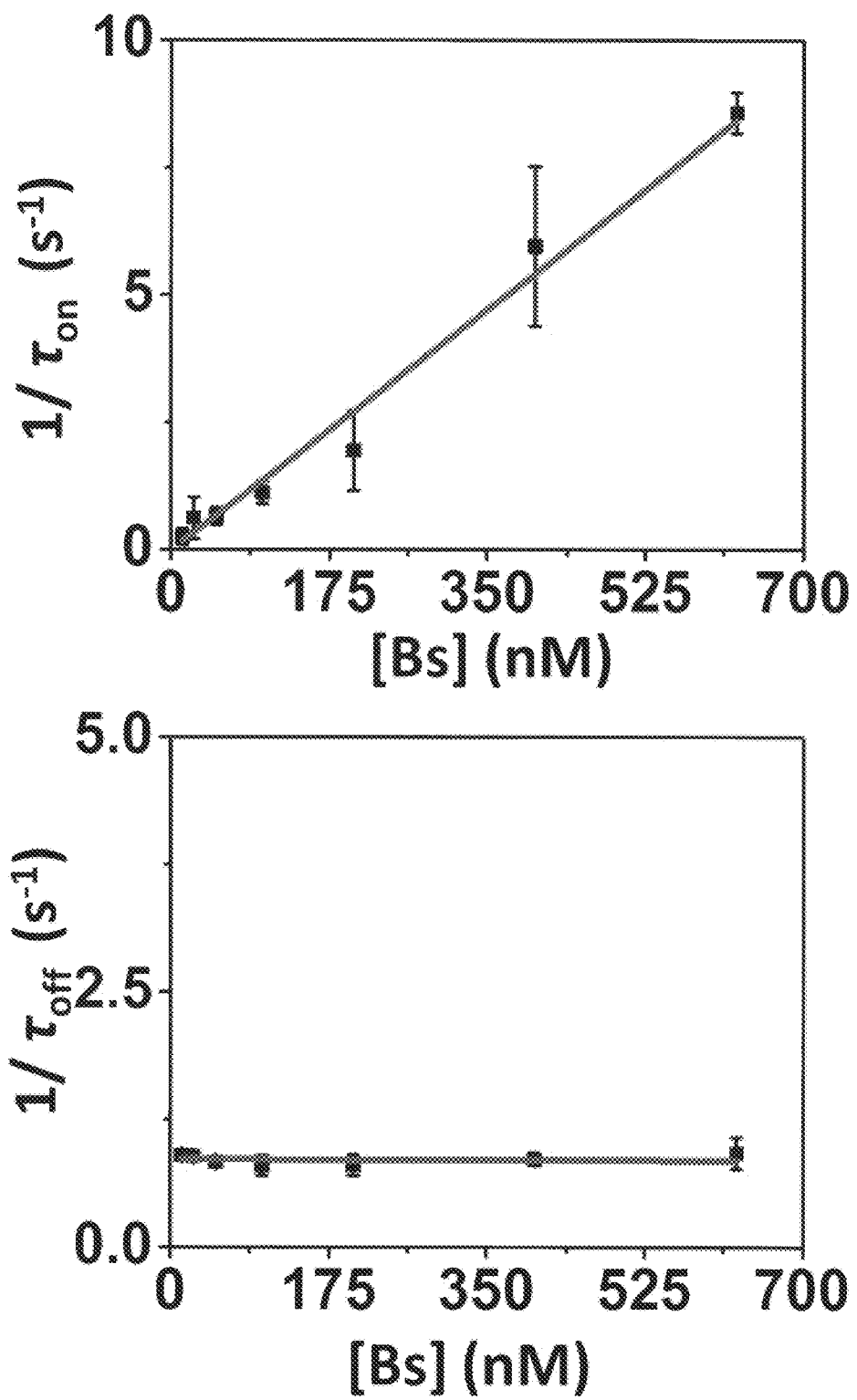
FIG. 5 is a series of graphs illustrating the dependence of $1/\tau_{on}$ and $1/\tau_{off}$ on the Bs concentration added to the cis side of the chamber.

It is worth mentioning that both the "on" and "off" events exhibited a single-exponential distribution function of their values, suggesting a single-barrier transition of the free-energy landscape of the PPIs. This conclusion was reached using a Logarithm Likelihood Ratio (LLR) test of the fitting models of these dwell-time histograms. The release "on" events decreased in duration, $\tau_{on}$, from 5054±2706 ms (n=3)

for 12.63 nM Bs to 595±300 ms (n=3) for 201.60 nM Bs (FIG. 3), confirming that the frequency of events was indeed dependent on the Bs concentration. On the contrary, we noted no change in the duration of the binding events, $\tau_{off}$, when the Bs concentration was altered (FIG. 4). For example, at a Bs concentration of 12.63 nM the binding events showed a duration of 1111±46 ms (n=3), whereas at a Bs concentration of 201.60 nM the binding events exhibited a duration of 1254±147 ms (n=3). Kinetic representation of release and binding events, as a function of Bs concentration within the cis side, was provided in FIG. 5. In FIG. 5, the reciprocal of the inter-event time interval, $\tau_{on}$, increases with increasing the concentration of the Bs protein analyte in the cis side of the chamber. The slope of the linear fit of $1/\tau_{on}$ versus the Bs concentration, [Bs], is exactly the association rate constant, $k_{on}$, of the binary Bn-Bs interactions, because $k_{on}=1/(\tau_{on}[Bs])$. In this case, $k_{on}=(1.59\pm0.01)\times10^7$ M$^{-1}$s$^{-1}$, with Adjusted R-square of ~1, confirming the fit quality. The $\tau_{off}$ binding time was independent of the concentration of the Bs protein analyte in the cis side of the chamber. The horizontal line is an average fit of the $(1/\tau_{off})$ data points recorded for various Bs concentration. The dissociation rate constant, $k_{off}$, is given by $k_{off}=1/\tau_{off}$. In this case, $k_{off}=0.973\pm0.053$ s$^{-1}$, which corresponds to a dissociation constant, $K_d$, of 61 nM This result is in excellent accord with prior kinetic determinations of the Bn-Bs interactions at various salt concentrations. For example, it was found by others that $k_{on}=\sim3\times10^7$ M$^{-1}$s$^{-1}$ in 300 NaCl, pH 8.0. On the other hand, it was determined that $k_{on}=\sim9.3\times10^7$ M$^{-1}$s$^{-1}$, $k_{off}=\sim0.23$ s$^{-1}$, and $K_d=\sim2.5$ nM at 100 NaCl, pH 8.0. An additional increase in the salt concentration (e.g., we used 300 mM KCl) is expected to further increase $k_{off}$ by several times. Moreover, the single-molecule approach of the present invention using an engineered protein nanopore sensor also indicated that the Bn-Bs interactions can be well approximated with a bimolecular interaction model. In this case, the frequency of the PPI events was in a nonlinear dependence on the protein concentration. This finding indicates the robustness of this method for quantitative assessment of high-affinity PPI.

The signal-to-noise ratio of the nanopore sensor was not affected at higher Bs concentration. The signal-to-noise ratio was not deteriorated by the substantial increase in the Bs concentration, although the single-molecule kinetic determinations of the binding event frequency were in a nonlinear regime (FIG. 10, FIG. 11). The experimentally acquired single-molecule data were fitted with a single exponential function:

$$\left(\frac{1}{\tau_{on}}\right)([Bs]) = \left(\frac{1}{\tau_{on}}\right)_{max}(1-e^{-R_0[Bs]}) \qquad (S1)$$

where $$\left(\frac{1}{\tau_{on}}\right)_{max} = 99 \pm 9 \text{ s}^{-1} \qquad (S2)$$

and $$R_0 = (1.80 \pm 0.25)\times 10^{-4} \text{M}^{-1} \qquad (S3)$$

Adjusted R-square=0.99, confirming the fit quality. Therefore, $$\left(\frac{1}{\tau_{on}}\right)([Bs] = 0) = 0 \qquad (S4)$$

$$\left(\frac{1}{\tau_{on}}\right)([Bs] = \infty) - \left(\frac{1}{\tau_{on}}\right)_{max} \qquad (S5)$$

In FIG. 11, the current noise of the single-channel electrical traces does not deteriorate at increased concentrations of the protein analyte. The applied transmembrane potential was −40 mV. Here, all single-channel electrical traces were low-pass Bessel filtered at 500 Hz. Other experimental conditions were the same as those mentioned in the caption of FIG. 2. For these measurements, we determined the following kinetic and thermodynamic parameters of the binding PPI interactions: $k_{on}=(1.1\pm0.1)\times10^7$ M$^{-1}$s$^{-1}$, $k_{off}=0.9$ s$^{-1}$, $K_d=82$ nM. It is worth mentioning that a slight increase in the dissociation constant, $K_d$, in the concentration nonlinear regime, was primarily caused by a decrease in the association rate constant, $k_{on}$. A small decrease in the $k_{off}$ rate constant, due to a small increase in the binding time, $\tau_{off}$, reduced that decrease in the $K_d$ dissociation constant at highly increased Bs concentrations At low micromolar concentrations of Bs, a slightly weaker binding interaction was probed with a dissociation constant, $K_d$, of ~82 nM, which resulted from a significant reduction in the $k_{on}$ rate constant, up to ~$1.1\times10^7$ M$^{-1}$s$^{-1}$, but a modest decrease in the $k_{off}$ rate constant, up to ~0.9 s$^{-1}$.

Real-time sampling of low-affinity PPI. Weak PPI, which feature $K_d$ values in the range of micromolar and even millimolar, are significant in many cell signaling pathways. The major difficulty in detecting and characterizing weak PPI arises from either high-dissociation or low-association rate constants, or both. To further explore the sensitivity of the OBn(GGS)$_2$t-FhuA sensor for much weaker PPI than those inspected above, single-channel electrical recordings were performed using D39A Bs, a homologous Bs variant with a much lower binding affinity. This weaker affinity of the Bn-D39A Bs complex was determined by the reduction in the electrostatic forces at the interaction interface. Indeed, when a low-nanomolar concentration of D39A Bs was added to the cis side, it was possible to observe reversible current transitions between the same O$_{on}$ and O$_{off}$ open substates, but with a binding duration in the low-millisecond scale. Thus, $\tau_{off}$ was much shorter than that value recorded with the Bn-Bs pair (FIG. 13A).

The frequency of the Bn-Bs binding events in the form of $1/\tau_{on}$ was linearly dependent on the Bs concentration, confirming a bimolecular association process (FIG. 13E). The slope of the linear fit of event frequency was the association rate constant, $k_{on}$. At the same time, the reciprocal of the $\tau_{off}$ duration, which is the dissociation rate constant, $k_{off}$, was independent of the Bs concentration, confirming a unimolecular dissociation process. $k_{on}=(1.34\pm0.04)\times10^7$ M$^{-1}$s$^{-1}$ and $k_{off}=0.86\pm0.02$ s$^{-1}$ was obtained, corresponding to an equilibrium dissociation constant, $K_d$, of 64±02 nM (Table 2 below). The value of this constant indicated a high-affinity PPI of the Bn-Bs pair.

TABLE 2

Association and dissociation rate constants as well as equilibrium dissociation constants for the transient Bn-Bs and Bn-D39A Bs interactions.

| Barstar Proteins | $k_{on} \times 10^{-7}$ (M$^{-1}$s$^{-1}$) | $k_{off}$ (s$^{-1}$) | $K_d$ (nM) |
|---|---|---|---|
| Bs | 1.34 ± 0.04 | 0.86 ± 0.02 | 64 ± 02 |
| D39A Bs | 0.193 ± 0.003 | 281 ± 8 | (146 ± 4) × 10$^3$ |

Values are the average ± SEM obtained from the curve fit of FIG. 13D and FIG. 14D. In this work, Bn was the H102A mutant of the wild-type barnase. In this way, the ribonuclease activity of barnase was abolished during its expression in *E. coli*. The other experimental conditions were the same as those stated in Table 1.

Again, the inter-event duration and dwell-time histograms showed single-exponential distribution functions, as illustrated by semi-logarithmic representations in FIG. 2B and FIG. 2C, respectively. This finding indicates a single energetic barrier for the single-molecule transitions between the release and binding substates of the low-affinity protein pair. The standard inter-event duration and dwell-time analyses of the corresponding "on" and "off" events are also shown in FIG. 16 and FIG. 17, respectively. $\tau_{on}$ decreased from ~2.4 s for 181.4 nM D39A Bs to ~360 ms for 1,440.6 nM D39A Bs (Table 3 below).

TABLE 3

The average values of the $\tau_{on}$ an $\tau_{off}$ time constants as well as the $k_{on}$ and $k_{off}$ kinetic rate constants for the transient Bn-D39A Bs interactions.

| [D39A Bs] (nM) | $\tau_{on}$ (ms) | $\tau_{off}$ (ms) | $k_{on}$ (M$^{-1}$s$^{-1}$) × 10$^{-7}$ | $k_{off}$ (s$^{-1}$) |
|---|---|---|---|---|
| 181.4 | 2,437 ± 1,216 | 3.6 ± 0.6 | 0.23 ± 0.11 | 287 ± 54 |
| 362.4 | 1,419 ± 614 | 3.8 ± 0.3 | 0.19 ± 0.08 | 267 ± 25 |
| 723.4 | 690 ± 169 | 3.6 ± 0.1 | 0.20 ± 0.05 | 276 ± 5 |
| 1,440.6 | 358 ± 105 | 3.8 ± 0.2 | 0.19 ± 0.06 | 266 ± 15 |

Values in the table are the average ± SD from at least 3 individual experiments. The other experimental conditions were the same as those stated in Table 1.

At the same time, no statistically significant alteration in $\tau_{off}$ was noted by changing the D39A Bs concentration. For example, $\tau_{off}$ was 3.6±0.6 ms (n=3) and 3.8±0.2 ms (n=3) for 181.4 and 1,440.6 nM D39A Bs, respectively. As noted above with the high-affinity Bs protein, the frequency of the low-affinity binding events also increased linearly by increasing the D39A Bs concentration (FIG. 13D). It was determined that the slope of this linear dependence was $k_{on}=(0.193±0.003)\times10^7$ M$^{-1}$s$^{-1}$ (Table 2). The weak PPI were characterized by a dissociation rate constant, $k_{off}$, of 281±8 s$^{-1}$, resulting in a $K_d$ of 146±4 µM. These findings are in accord with the earlier studies performed in bulk phase. For example, in 50 mM Tris·HCl, pH 8, these transient PPI between Bn and D39A Bs featured the $k_{off}$ and $K_d$ values of ~17 s$^{-1}$ and ~39 nM, respectively. These PPI were about two orders of magnitude weaker than those recorded between Bn and Bs, which exhibited a $K_d$ of ~0.32 nM under the same experimental conditions. This outcome indicates the capability of the OBn(GGS)$_2$t-FhuA sensor to detect short-lived PPI at protein ligand concentrations several orders of magnitude below its respective $K_d$. Resolving the transient PPI at a millisecond-time resolution is challenging when using other biophysical methods in solution. Conversely, this nanopore sensor shows prospects for studying kinetics of weak PPI without technical shortcomings of other prevailing approaches, including low signal-to-noise ratio and high $k_{off}$ value.

Concurrent detection of weak and strong PPI. Simultaneous fingerprinting of more than one protein analyte in a given composite mixture of proteins is an attractive feature of any diagnostic tool. Therefore, in a follow-up experiment, simultaneous sampling of low- and high-affinity protein ligands in solution was examined. The concomitant presence of Bs and D39A Bs in solution produced both long-lived and brief current transitions observed with individual proteins, respectively (FIG. 14A). For instance, when 25 nM Bs and 1,440 nM D39A Bs were added to the cis side both the long-lived and brief current transitions were detected with durations of 936±38 ms (n=3) and 4.0±0.3 ms (n=3), respectively (FIG. 14B; Tables 4 and 5 below).

TABLE 4

Probability, dwell time, and frequency of the PPI events for Bn-Bs interaction in presence of two homologous Bs variants, D39A Bs and Bs.

| [D39A Bs] and [Bs] (nM) | Probability$_{Bs}$ | $k_{off\text{-}Bs}$ (s$^{-1}$) | FOE$_{Bs}$ (s$^{-1}$) | $\tau_{off\text{-}Bs}$ (ms) |
|---|---|---|---|---|
| 1,440 and 25 | 0.049 ± 0.001 | 1.07 ± 0.04 | 0.14 ± 0.04 | 936 ± 38 |
| 1,439 and 100 | 0.211 ± 0.079 | 1.11 ± 0.09 | 0.46 ± 0.11 | 905 ± 69 |
| 1,435 and 399 | 0.475 ± 0.096 | 1.09 ± 0.09 | 0.58 ± 0.11 | 914 ± 79 |

FOE indicates the event frequency. Values in the table are the average ± SD (n = 3). The other experimental conditions were the same as those stated in Table 1.

TABLE 5

Probability, dwell time, and frequency of the PPI events for Bn-D39A Bs interactions in presence of two homologous Bs variants, D39A Bs and Bs.

| [D39A Bs] and [Bs] (nM) | Probability$_{D39A\,Bs}$ | $k_{off\text{-}D39A\,Bs}$ (s$^{-1}$) | FOE$_{D39A\,Bs}$ (s$^{-1}$) | $\tau_{off\text{-}D39A\,Bs}$ (ms) |
|---|---|---|---|---|
| 1,440 and 25 | 0.951 ± 0.001 | 249 ± 17 | 2.6 ± 0.8 | 4.0 ± 0.3 |
| 1,439 and 100 | 0.787 ± 0.079 | 261 ± 42 | 1.8 ± 0.6 | 3.9 ± 0.7 |
| 1,435 and 399 | 0.525 ± 0.096 | 268 ± 51 | 0.65 ± 0.22 | 3.8 ± 0.8 |

FOE indicates the event frequency. Values in the table are the average ± SD (n = 3). The other experimental conditions were the same as those stated in Table 1.

Gradual increase in the concentration of the high-affinity Bs resulted in an enhancement in the frequency of long-lived current transitions and a drastic reduction in the frequency of the brief Bn-D39A Bs binding events. For example, by increasing the Bs concentration from 25 to 399 nM, the frequency of long-lived Bn-Bs binding events changed from 0.14±0.04 to 0.58±0.11 s$^{-1}$. Conversely, the frequency of the brief Bn-D39A Bs binding events decreased from 2.6±0.8 to 0.65±0.22 s$^{-1}$. These experiments revealed the selective nature of this PPI nanopore sensor by the quantitative evaluation of the competitive interactions among two homologous Bs variants against the same binding site. Therefore, this approach might be extended for the disentanglement of more complex readouts resulting from multiple and concurrent PPI of protein mixtures in solution.

Single-molecule detection of proteins and quantitation of the PPI kinetics in a complex biofluid sample. Perhaps the most promising aspect of any diagnostic tool is its capability to detect and accurately quantitate a given protein target in a complex biofluid sample, such as mammalian serum and urine. Likewise, kinetic determinations of the transient PPI are challenging under these conditions. Hence, the capability of the OBn(GGS)$_2$t-FhuA sensor for Bs detection was tested in the presence of unprocessed, mammalian fetal bovine serum (FBS). When Bs was not present in the chamber, OBn(GGS)$_2$t-FhuA exhibited a uniform and quiet unitary current at a transmembrane potential of −15 mV. Its recorded value was 19.9±1.1 pA (n=3) (FIG. 15A; upper trace). Single-channel electrical traces acquired with OBn(GGS)$_2$t-FhuA in the presence of 12.6 nM Bs, which was added to the cis side, displayed reversible low-current amplitude transitions between $O_{on}$ (−19.7±0.2 pA; n=3) and $O_{off}$ (−22.6±0.2 pA; n=3) open substates (FIG. 15A; middle trace). In the presence of 5% (v/v) FBS, large-amplitude current blockades were recorded, more likely produced by the serum constituents that partitioned into the pore lumen ($I_{FBS}$; FIG. 15A; bottom trace). Remarkably, under these experimental conditions the single-channel electrical traces also showed low-amplitude, PPI-induced current transitions that were unambiguously distinguished from large-amplitude current blockades. The FBS-produced current blockades corresponded to all-points histogram peaks at current values of −12.0±0.7 and −3.4±0.2 pA (n=3) (FIG. 15B). Here, a voltage value of −15 mV was chosen, because at a greater transmembrane potential of −40 mV the FBS-produced current blockades were very long (see FIG. 18). These long-lived blockades precluded a precise evaluation of the kinetic rate constants. Notably, the transient PPI recorded at transmembrane potentials of −15 and −40 mV displayed no statistically significant distinctions in kinetic rate constants (Tables 1, 2, and 6).

TABLE 6

The average values of the $\tau_{on}$ and $\tau_{off}$ time constants as well as the $k_{on}$ and $k_{off}$ kinetic rate constants for the transient Bn-Bs interactions in the absence and presence of FBS.

| 5% FBS | $\tau_{on}$ (ms) | $\tau_{off}$ (ms) | $k_{on}$ (M$^{-1}$s$^{-1}$) × 10$^{-7}$ | $k_{off}$ (s$^{-1}$) |
|---|---|---|---|---|
| − | 4,635 ± 1,472 | 1,323 ± 171 | 1.71 ± 0.54 | 0.76 ± 0.09 |
| + | 6,358 ± 2,906 | 1,145 ± 18 | 1.25 ± 0.57 | 0.87 ± 0.01 |

Values in the table are the average ± SD ( −FBS; n = 6 +FBS; n = 3). In this work, Bn was the H102A mutant of the wild-type barnase. In this way, the ribonuclease activity of barnase was abolished during its expression in E. coli. The applied transmembrane potential was −15 mV. The buffer solution contained 12.6 nM Bs, 300 mM KCl, 10 mM Tris•HCl, pH 8. All experiments were conducted at a temperature of 23 ± 1° C.

Interestingly, the FBS-produced current alterations returned to the original open substate of departure. For example, a current blockade leaving the $O_{off}$ substate returned to the $O_{off}$ substate as well. The same process also occurred in the case of the FBS-produced transitions that originated from the $O_{on}$ substate (release level). This finding suggests that the partitioning of serum constituents into the pore lumen is independent of the binding-release events of the Bn-Bs complex at a transmembrane potential of −15 mV. Furthermore, this outcome eased the analyses of the inter-event durations and dwell times in the presence of FBS. Representative standard histograms, which were acquired in the absence and presence and of 5% (v/v) FBS, are displayed in FIG. 15C and FIG. 15D, respectively.

It is worth mentioning that the kinetic rate constants of the transient PPI in the absence and presence of FBS were closely similar. For instance, $k_{on}$ values of (1.71±0.54)×10$^7$ M$^{-1}$s$^{-1}$ (n=6) and (1.25±0.57)×10$^7$M$^{-1}$s$^{-1}$ (n=3) were acquired, respectively, when 12.6 nM Bs was added to the cis side (Table 6). The $k_{off}$ values were 0.76±0.09 s$^{-1}$ (n=6) and 0.87±0.01 s$^{-1}$ (n=3), respectively. To test the sensitivity of this single-molecule sensor, the Bs concentration in was assayed in the presence of FBS using $C_{Bs}=1/(\tau_{on}k_{on})$, where $C_{Bs}$, $\tau_{on}$, and $k_{on}$ are the concentration of the targeted Bs protein, inter-event duration determined in the presence of FBS, and association rate constant inferred for Bs in the absence of FBS, respectively. The average Bs concentration was 13.3±5.0 nM (n=3). This value agrees with the actual concentration of 12.6 nM Bs added to the cis chamber. Therefore, this nanopore sensor has the capability to detect and quantitate a targeted protein analyte in a biological fluid sample. In addition, detailed kinetic information of the transient PPI can be accurately gained under these challenging conditions.

Development of a genetically-encoded t-FhuA sensor for transient PPI. The outcomes of this study suggest that Bn was indeed located outside the pore lumen and on the β-turns' side of t-FhuA.

Therefore, there is no technical challenge in replacing Bn with another protein receptor of comparable or even greater size and there is no fundamental limitation in substituting Bs with other protein ligands. With further development, our method might be extended for analytical assessment of the PPI systems involved in cell signaling and cancer development, such as those mediated by the Ras GTPase and constitutively active serine-threonine kinases (e.g., Pim and CK2). The fact that Bn and t-FhuA are located in fairly well-separated water-soluble and hydrophobic phases, respectively, can be advantageously employed for their concurrent refolding in detergent micelles. In the past, numerous detergents, buffer conditions, and refolding approaches were tested for optimizing the pore-forming ability, protein folding, and uniformity of the unitary conductance of various truncation FhuA derivatives. It is critical that any chosen refolding protocol should not impair the pore-forming ability of this genetically-encoded sensor. A stable open-state conductance is a major step for the successful determination of the kinetics and energetics of the binding events. However, difficulties in acquiring accurate values of the kinetic rate constants might arise if an elongated protein receptor is used, whose binding surface is at a distant location from the pore opening.

The PPI example was exclusively focused on a well-studied Bn-Bs interacting pair with 110- and 89-residue proteins. The average diameter of a 100-residue globular protein (~12 kDa) is ~3.2 nm, whereas a 400-residue protein (~48 kDa) has diameter ~5.1 nm. Therefore, this approach might be used for tethering monomeric proteins with a size in this range, given the relatively small change in average hydrodynamic diameter. Different protein sizes might also require tuning the length of the flexible peptide tether, facilitating a clearance of the space near the pore opening. An optimized length of the flexible peptide tether would enable accessibility of the receptor binding site to the protein ligand. On the other hand, a rigid peptide tether and a restrained exposure of the receptor binding site would likely affect the kinetic rate constants of association and dissociation. The receptor-ligand complex formation must also result in a specific conformational alteration of the receptor, which is pulled away from the pore opening.

Quantitative and qualitative comparisons with other competing technologies. Most biophysical approaches for the quantification of kinetics and energetics of transient PPI are conducted in bulk phase. Thus, they are restrained to the average determination of an ensemble of proteins in solution. In contrast, our method will potentially enable the detection and characterization of subpopulations of distinctive binding events, which are unachievable by prevailing techniques. Furthermore, this genetically-encoded sensor shows promise for the identification of rare and very brief binding events (e.g., low-affinity PPI) that are hidden by traditional recording technologies in bulk phase. A powerful feature of this approach is that temperature-dependent electrical recordings might be pursued to illuminate the enthalpic and entropic contributions to the kinetic rate constants of association and dissociation of transient PPI.

Simultaneous determination of the $k_{off}$ values for more than one protein target, while providing the apparent $k_{on}$'s and IC$_{50}$, is quite a challenging task using other techniques in solution. Using our single-molecule nanopore sensor one cannot only fingerprint multiple protein targets at once, but also can study the competitive nature of their interactions against the same binding site. This competitive-binding process relates to numerous cell signaling pathways. For example, this approach might be employed for quantitative assessment of more complex signals resulting from composite mixtures of interacting partners, in which case one receptor concomitantly interacts with other substrates, effectors, and regulatory proteins. Therefore, these kinetic determinations would facilitate an integrated overview of a complex PPI network involved in cell signaling under normal and oncogenic conditions.

Biolayer interferometry (BLI) and surface plasmon resonance (SPR) have been used in the affinity, kinetic, and thermodynamic determinations of transient PPI in bulk phase. Likewise, these are real-time techniques, which are amenable to a high-throughput setting and coupling with protein-array screenings. SPR must be cautiously employed in kinetic binding measurements due to a number of daunting challenges, including nonspecific protein binding on surfaces, surface heterogeneity, rebinding, protein inactivation at the liquid-metal film interface, molecular crowding effects, and problems associated with multiple binding sites and mass transport. On the other hand, examination of the binding kinetics using isothermal titration calorimetry (ITC) is not high throughput and necessitates large quantities of proteins. It should be noted that BLI, SPR, and ITC provide average kinetic or affinity parameters and they cannot be used in a heterogeneous sample. These techniques do not offer information regarding the distributions of substrate populations as a result of potential obstructions to protein binding (e.g., crowding agents). In contrast, our single-molecule approach is likely to work in a more complex, heterogeneous sample.

Finally, our method has a high temporal resolution and capabilities for a broad range of kinetic rate constants, because it relies on a single-molecule protein detector. Under extreme conditions pertaining to unusually high association rate constants, such as those in the range of $10^7$-$10^8$ $M^{-1}s^{-1}$, our approach can directly probe such values. In stochastic sensing, $k_{off}$ and $k_{on} \times$[analyte] can be directly measured up to a value of ~$10^4$ $s^{-1}$. Here, it was demonstrated that this nanopore sensor can probe $k_{off}$ in the range of $10^2$-$10^3$ $s^{-1}$ and there is no expected technical challenge to resolve even shorter PPI events, which have a faster dissociation rate constant. This capability has practical significance, because of the pressing need for quantitative characterization of extremely weak PPI involved in the rapid responses of cell signaling pathways.

The present invention is the first protein pore-based nanostructure for the stochastic sampling of reversible PPI in solution at single-molecule resolution. The outcomes of these studies using the specific Bn-Bs pair of interacting partners revealed that the binding PPIs occurred with a single rate constant of dissociation. Advantageous features of this protein pore-based nanostructure include the following: (i) the sequence of binding and release events, which occur at equilibrium, can be unambiguously observed by discrete current transitions between well-separated open states of the OBa(GGS)$_2$t-FhuA protein pore; (ii) the truncation t-FhuA protein is monomeric, so that its molecular engineering with atomic precision was achieved as a single-chain pore-forming polypeptide without the need for tedious and lengthy purification steps of targeted oligomer from other products of the assembly reaction, otherwise a path required for a multimeric protein complex; (iii) this bioinspired pore-based nanostructure was obtained as a single fusion polypeptide, encompassing different functional domains, and without the need for chemical modification (e.g., the covalent attachment of the protein receptor element at a site of the pore lumen); (iv) t-FhuA is an expressible outer membrane protein system in E. coli, tolerating both extensive charge alterations within the pore lumen as well as folded protein domains on the periplasmic side without deteriorating the signal-to-noise ratio or stability of the open-state current; (v) the OBa(GGS)$_2$t-FhuA protein pore confirmed a vectorial insertion into a lipid membrane with a preferred orientation, outperforming other membrane protein systems, which insert into a membrane with a random orientation; this a significant trait of this pore-based nanostructure, because is can be used in molecular medical biotechnology in a controlled fashion; (vi) the PPI events occurred outside the pore lumen, so that not within the voltage-drop region of the protein, which otherwise might affect the intrinsic binding interactions and even protein folding. In addition, sensing outside the pore lumen would enable the protein recognition element to sample exactly how much protein ligand navigates around the binding site of the recognition protein, because there is no steric restriction of this interaction, otherwise observed with other systems; (vii) the resolution of the current transitions between the binding ($O_{off}$) and unbinding ($O_{on}$) states enables the kinetic and energetic determinations at physiological ion concentrations; (viii) the transient PPI interactions are recorded in real time and without the need of fluorescence labeling of either of the protein partners; (ix) the substantial increase in the concentration of the protein analyte within the chamber does not deteriorate signal-to-noise ratio or the stability of the open state current; (x) the t-FhuA protein scaffold, which serves as an event transducer, exhibits an unusual robustness under various harsh environmental, physical or chemical conditions of sensing. This robustness will allow the extensive explorations of the PPIs in a broad range of experimental circumstances.

The use of such a protein nanostructure will certainly be instrumental in developing a novel knowledge of PPIs by providing the kinetics and energetics of intermolecular forces between various protein partners. Therefore, such an engineered pore-based protein nanostructure might have a potentially transformative impact in the broad area of nanoproteomics and protein biotechnology. This approach might be used to unravel various aspects, including high-throughput screening (HTS) of small-molecule drugs, peptide inhibitors, and other physical and chemical factors that modulate these interactions. In addition, such a pore-based nanostructure might be employed to examine the effect of post-translational modifications to the stability and specificity of such PPIs. Although the primary focus of this example of the present invention was illustrating the advantageous features of this engineered protein for the detailed kinetic examination of the transient PPIs, its great prospects as a stochastic sensing element for protein detection and analysis at single-molecule resolution must also be emphasized. Moreover, there is no fundamental limitation in replacing the protein recognition sensing element with another protein receptor and there is no technical challenge in substituting the Bs protein analyte with other binding protein domain. Finally, such nanostructure prototype might represent a precursor for the development of more automated, HTS screening of protein biomarkers using microfabricated protein arrays, as well as kinetic analysis of new non-antibody recognition proteins.

The use of such a protein nanostructure might be instrumental in novel chemical biology research by providing the kinetics and energetics of intermolecular forces between various protein partners. Notably, our approach permits the detection and detailed kinetic characterization of PPI at protein ligand concentrations of several orders of magnitude either below or above the $K_d$. This sensing enabled us to sample exactly how much protein ligand navigated around the binding site of the protein receptor, because there was no steric restriction of this interaction. The molecular engineering of this PPI sensor with atomic precision was achieved as a single-chain pore-forming polypeptide. Therefore, there was no requirement for chemical attachment of fluorophores or tedious purification steps of targeted oligomer from other products of the assembly reaction, like many other multimeric protein nanopores necessitate. The single-polypeptide chain composition of this genetically-encoded nanostructure enables the design and development of combinatorial sensor libraries containing various protein receptors. Moreover, this nanopore sensor has a vectorial insertion into a lipid membrane with a preferred orientation, showing promise for its functional reconstitution in a controlled fashion. This PPI sensing prototype might have a potentially transformative impact in the areas of clinical nanoproteomics and protein biotechnology. For example, this approach might be used for the high-throughput screening of small-molecule drugs, peptide inhibitors, or other physical and chemical factors that modulate the transient PPI. This nanopore sensor might be employed to examine the effect of post-translational modifications to the stability and specificity of such PPI. Finally, the ability to distinguish a specific PPI readout from other nonspecific or false-positive complex signals of a biological fluid sample shows realistic prospects of the receptor-containing t-FhuA sensor for single-molecule protein detection in cell lysates, biopsies, and blood stream.

The invention claimed is:

1. A protein sensor, comprising:
a membrane;
a transducer positioned in the membrane;
a protein receptor tethered to the transducer by a flexible linker;
a charged polypeptide adaptor coupled to the protein receptor, wherein the charged polypeptide adaptor comprises SEQ. ID NO. 4.

2. The protein sensor of claim 1, wherein the flexible linker comprises SEQ. ID. NO. 2.

3. The protein sensor of claim 2, wherein the protein receptor is tethered to an N terminus of the transducer.

4. A protein sensor, comprising:
a membrane;
a transducer positioned in the membrane;
a protein receptor tethered to the transducer by a flexible linker, wherein the transducer comprises SEQ. ID. NO. 1;
a charged polypeptide adaptor coupled to the protein receptor.

5. The protein sensor of claim 1, wherein the membrane divides a chamber into a cis side and a trans side.

6. The protein sensor of claim 5, wherein the transducer is positioned in the membrane so that an N terminus and a C terminus of the transducer are positioned in the cis side of the chamber.

7. The protein sensor of claim 1, wherein the addition of a protein target that interacts with the protein receptor into the cis side of the chamber will produce a reversible current transition across the membrane.

8. The protein sensor of claim 7, wherein the reversible current transition across the membrane reflects an interaction between the protein receptor and the protein target and a concentration of the protein target.

9. The protein sensor of claim 8, wherein the reversible current transition comprises a reduction in current flowing across the membrane when a predetermined voltage is established across the membrane.

10. A method of detecting a protein-protein interaction, comprising the steps of:
providing a protein sensor having a membrane dividing a chamber into a cis side and a trans side, a transducer positioned in the membrane so that an N terminus and a C terminus of the transducer is position in the cis side of the chamber, a protein receptor tethered to the N terminus of the transducer by a flexible linker, and a charged polypeptide adaptor coupled to the protein receptor, wherein the charged polypeptide adaptor comprises SEQ. ID NO. 4;
adding a protein target to the protein sensor that will interact with the protein receptor into the cis side of the chamber; and
detecting with the transducer whether there is a reversible current transition across the membrane in response to adding the protein target to the cis side of the chamber.

11. The method of claim 10, wherein the reversible current transition across the membrane reflects an interaction between the protein receptor and the protein target and a concentration of the protein target.

12. The method of claim 1, wherein the flexible linker comprises SEQ. ID NO: 2.

13. The method of claim 12, wherein the transducer comprises SEQ. ID. NO. 1.

* * * * *

SEQUENCE LISTING

```
<160> NUMBER OF SEQ ID NOS: 13

<210> SEQ ID NO 1
<211> LENGTH: 455
<212> TYPE: PRT
<213> ORGANISM: Escherichia coli

<400> SEQUENCE: 1

Leu Lys Glu Val Gln Phe Lys Ala Gly Thr Asp Ser Leu Phe Gln Thr
1               5                   10                  15

Gly Phe Asp Phe Ser Asp Ser Leu Asp Asp Gly Val Tyr Ser Tyr
            20                  25                  30

Arg Leu Thr Gly Leu Ala Arg Ser Ala Asn Ala Gln Gln Lys Gly Ser
        35                  40                  45

Glu Glu Gln Arg Tyr Ala Ile Ala Pro Ala Phe Thr Trp Arg Pro Asp
    50                  55                  60

Asp Lys Thr Asn Phe Thr Phe Leu Ser Tyr Phe Gln Asn Glu Pro Glu
65                  70                  75                  80

Thr Gly Asn Ser Glu Gly Ser Thr Tyr Ser Arg Asn Glu Lys Met Val
                85                  90                  95

Gly Tyr Ser Phe Asp His Glu Phe Asn Asp Thr Phe Thr Val Arg Gln
            100                 105                 110

Asn Leu Arg Phe Ala Glu Asn Lys Thr Ser Gln Asn Ser Val Tyr Gly
        115                 120                 125

Asn Ser Glu Gly Ser Arg Lys Tyr Val Val Asp Asp Glu Lys Leu Gln
    130                 135                 140

Asn Phe Ser Val Asp Thr Gln Leu Gln Ser Lys Phe Ala Thr Gly Asp
145                 150                 155                 160

Ile Asp His Thr Leu Leu Thr Gly Val Asp Phe Met Arg Met Arg Asn
                165                 170                 175

Asp Ile Asn Ala Trp Phe Gly Tyr Asn Ser Glu Gly Ser Ser Gly Pro
            180                 185                 190

Tyr Arg Ile Leu Asn Lys Gln Lys Gln Thr Gly Val Tyr Val Gln Asp
        195                 200                 205

Gln Ala Gln Trp Asp Lys Val Leu Val Thr Leu Gly Gly Arg Tyr Asp
    210                 215                 220

Trp Ala Asp Gln Glu Ser Leu Asn Arg Val Ala Gly Thr Thr Asp Lys
225                 230                 235                 240

Arg Asp Asp Lys Gln Phe Thr Trp Arg Gly Gly Val Asn Tyr Leu Phe
```

```
                        245                 250                 255
Asp Asn Gly Val Thr Pro Tyr Phe Ser Tyr Ser Glu Ser Phe Glu Pro
            260                 265                 270

Ser Ser Gln Val Gly Lys Asp Gly Asn Ile Phe Ala Pro Ser Lys Gly
            275                 280                 285

Lys Gln Tyr Glu Val Gly Val Lys Tyr Val Pro Glu Asp Arg Pro Ile
            290                 295                 300

Val Val Thr Gly Ala Val Tyr Asn Leu Thr Lys Thr Asn Asn Leu Met
305                 310                 315                 320

Ala Asp Pro Glu Gly Ser Phe Phe Ser Val Glu Gly Glu Ile Arg
            325                 330                 335

Ala Arg Gly Val Glu Ile Glu Ala Lys Ala Ala Leu Ser Ala Ser Val
            340                 345                 350

Asn Val Val Gly Ser Tyr Thr Tyr Thr Asp Ala Glu Tyr Thr Thr Asp
            355                 360                 365

Thr Thr Tyr Lys Gly Asn Thr Pro Ala Gln Val Pro Lys His Met Ala
            370                 375                 380

Ser Leu Trp Ala Asp Tyr Thr Phe Phe Asp Gly Pro Leu Ser Gly Leu
385                 390                 395                 400

Thr Leu Gly Thr Gly Gly Arg Tyr Thr Asn Ser Glu Gly Ser Tyr Thr
            405                 410                 415

Val Val Asp Ala Leu Val Arg Tyr Asp Leu Ala Arg Val Gly Met Ala
            420                 425                 430

Gly Ser Asn Val Ala Leu His Val Asn Ser Glu Gly Ser Gln Val Val
            435                 440                 445

Ala Thr Ala Thr Phe Arg Phe
            450                 455

<210> SEQ ID NO 2
<211> LENGTH: 6
<212> TYPE: PRT
<213> ORGANISM: Artificial Sequence
<220> FEATURE:
<223> OTHER INFORMATION: Peptide linker

<400> SEQUENCE: 2

Gly Gly Ser Gly Gly Ser
1               5

<210> SEQ ID NO 3
<211> LENGTH: 109
<212> TYPE: PRT
<213> ORGANISM: Artificial Sequence
<220> FEATURE:
<223> OTHER INFORMATION: Protein receptor

<400> SEQUENCE: 3

Met Val Ile Asn Thr Phe Asp Gly Val Ala Asp Tyr Leu Gln Thr Tyr
1               5                   10                  15

His Lys Leu Pro Asp Asn Tyr Ile Thr Lys Ser Glu Ala Gln Ala Leu
            20                  25                  30

Gly Trp Val Ala Ser Lys Gly Asn Leu Ala Asp Val Ala Pro Gly Lys
            35                  40                  45

Ser Ile Gly Gly Asp Ile Phe Ser Asn Arg Glu Gly Lys Leu Pro Gly
            50                  55                  60

Lys Ser Gly Arg Thr Trp Arg Glu Ala Asp Ile Asn Tyr Thr Ser Gly
65                  70                  75                  80
```

```
Phe Arg Asn Ser Asp Arg Ile Leu Tyr Ser Ser Asp Trp Leu Ile Tyr
                85                  90                  95

Lys Thr Thr Asp Ala Tyr Gln Thr Phe Thr Lys Ile Arg
            100                 105

<210> SEQ ID NO 4
<211> LENGTH: 12
<212> TYPE: PRT
<213> ORGANISM: Artificial Sequence
<220> FEATURE:
<223> OTHER INFORMATION: Polypeptide adaptor

<400> SEQUENCE: 4

Met Gly Asp Arg Gly Pro Glu Phe Glu Leu Gly Thr
1               5                   10

<210> SEQ ID NO 5
<211> LENGTH: 582
<212> TYPE: PRT
<213> ORGANISM: Artificial Sequence
<220> FEATURE:
<223> OTHER INFORMATION: Sensor

<400> SEQUENCE: 5

Met Gly Asp Arg Gly Pro Glu Phe Glu Leu Gly Thr Met Val Ile Asn
1               5                   10                  15

Thr Phe Asp Gly Val Ala Asp Tyr Leu Gln Thr Tyr His Lys Leu Pro
            20                  25                  30

Asp Asn Tyr Ile Thr Lys Ser Glu Ala Gln Ala Leu Gly Trp Val Ala
            35                  40                  45

Ser Lys Gly Asn Leu Ala Asp Val Ala Pro Gly Lys Ser Ile Gly Gly
        50                  55                  60

Asp Ile Phe Ser Asn Arg Glu Gly Lys Leu Pro Gly Lys Ser Gly Arg
65                  70                  75                  80

Thr Trp Arg Glu Ala Asp Ile Asn Tyr Thr Ser Gly Phe Arg Asn Ser
                85                  90                  95

Asp Arg Ile Leu Tyr Ser Ser Asp Trp Leu Ile Tyr Lys Thr Thr Asp
                100                 105                 110

Ala Tyr Gln Thr Phe Thr Lys Ile Arg Gly Gly Ser Gly Gly Ser Leu
            115                 120                 125

Lys Glu Val Gln Phe Lys Ala Gly Thr Asp Ser Leu Phe Gln Thr Gly
        130                 135                 140

Phe Asp Phe Ser Asp Ser Leu Asp Asp Asp Gly Val Tyr Ser Tyr Arg
145                 150                 155                 160

Leu Thr Gly Leu Ala Arg Ser Ala Asn Ala Gln Gln Lys Gly Ser Glu
                165                 170                 175

Glu Gln Arg Tyr Ala Ile Ala Pro Ala Phe Thr Trp Arg Pro Asp Asp
            180                 185                 190

Lys Thr Asn Phe Thr Phe Leu Ser Tyr Phe Gln Asn Glu Pro Glu Thr
            195                 200                 205

Gly Asn Ser Glu Gly Ser Thr Tyr Ser Arg Asn Glu Lys Met Val Gly
        210                 215                 220

Tyr Ser Phe Asp His Glu Phe Asn Asp Thr Phe Thr Val Arg Gln Asn
225                 230                 235                 240

Leu Arg Phe Ala Glu Asn Lys Thr Ser Gln Asn Ser Val Tyr Gly Asn
                245                 250                 255

Ser Glu Gly Ser Arg Lys Tyr Val Val Asp Asp Glu Lys Leu Gln Asn
            260                 265                 270
```

-continued

```
Phe Ser Val Asp Thr Gln Leu Gln Ser Lys Phe Ala Thr Gly Asp Ile
        275                 280                 285

Asp His Thr Leu Leu Thr Gly Val Asp Phe Met Arg Met Arg Asn Asp
    290                 295                 300

Ile Asn Ala Trp Phe Gly Tyr Asn Ser Glu Gly Ser Ser Gly Pro Tyr
305                 310                 315                 320

Arg Ile Leu Asn Lys Gln Lys Gln Thr Gly Val Tyr Val Gln Asp Gln
                325                 330                 335

Ala Gln Trp Asp Lys Val Leu Val Thr Leu Gly Gly Arg Tyr Asp Trp
            340                 345                 350

Ala Asp Gln Glu Ser Leu Asn Arg Val Ala Gly Thr Thr Asp Lys Arg
        355                 360                 365

Asp Asp Lys Gln Phe Thr Trp Arg Gly Gly Val Asn Tyr Leu Phe Asp
    370                 375                 380

Asn Gly Val Thr Pro Tyr Phe Ser Tyr Ser Glu Ser Phe Glu Pro Ser
385                 390                 395                 400

Ser Gln Val Gly Lys Asp Gly Asn Ile Phe Ala Pro Ser Lys Gly Lys
                405                 410                 415

Gln Tyr Glu Val Gly Val Lys Tyr Val Pro Glu Asp Arg Pro Ile Val
            420                 425                 430

Val Thr Gly Ala Val Tyr Asn Leu Thr Lys Thr Asn Asn Leu Met Ala
        435                 440                 445

Asp Pro Glu Gly Ser Phe Phe Ser Val Glu Gly Gly Glu Ile Arg Ala
    450                 455                 460

Arg Gly Val Glu Ile Glu Ala Lys Ala Ala Leu Ser Ala Ser Val Asn
465                 470                 475                 480

Val Val Gly Ser Tyr Thr Tyr Thr Asp Ala Glu Tyr Thr Thr Asp Thr
                485                 490                 495

Thr Tyr Lys Gly Asn Thr Pro Ala Gln Val Pro Lys His Met Ala Ser
            500                 505                 510

Leu Trp Ala Asp Tyr Thr Phe Phe Asp Gly Pro Leu Ser Gly Leu Thr
        515                 520                 525

Leu Gly Thr Gly Gly Arg Tyr Thr Asn Ser Glu Gly Ser Tyr Thr Val
    530                 535                 540

Val Asp Ala Leu Val Arg Tyr Asp Leu Ala Arg Val Gly Met Ala Gly
545                 550                 555                 560

Ser Asn Val Ala Leu His Val Asn Ser Glu Gly Ser Gln Val Val Ala
                565                 570                 575

Thr Ala Thr Phe Arg Phe
            580

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
gagcggtctc caatggttat caacacgttt                                    30

<210> SEQ ID NO 7
<211> LENGTH: 36
<212> TYPE: DNA
<213> ORGANISM: Artificial Sequence
<220> FEATURE:
```

<223> OTHER INFORMATION: Primer

<400> SEQUENCE: 7
caggctgccg ctgccgcctc tgatttttgt aaaggt                                36

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
agaggcggca gcggcggcag cctgaaagaa gttcag                                36

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
ccgcgcgtac cttaaaaacg aaaggtt                                          27

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
catggtacca tggttatcaa cacgtttga                                        29

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
atcggtctcc aatgaaaaaa gca                                              23

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
agcggtctcc gcgctttaag aaagtatgat ggt                                   33

<210> SEQ ID NO 13
<211> LENGTH: 90
<212> TYPE: PRT
<213> ORGANISM: Bacillus amyloliquefaciens

<400> SEQUENCE: 13

Met Lys Lys Ala Val Ile Asn Gly Glu Gln Ile Arg Ser Ile Ser Asp
1               5                   10                  15

Leu His Gln Thr Leu Lys Lys Glu Leu Ala Leu Pro Glu Tyr Tyr Gly
            20                  25                  30

-continued

```
Glu Asn Leu Asp Ala Leu Trp Asp Ala Leu Thr Gly Trp Val Glu Tyr
        35                  40                  45
Pro Leu Val Leu Glu Trp Arg Gln Phe Glu Gln Ser Lys Gln Leu Thr
        50                  55                  60
Glu Asn Gly Ala Glu Ser Val Leu Gln Val Phe Arg Glu Ala Lys Ala
65              70                  75                  80
Glu Gly Ala Asp Ile Thr Ile Ile Leu Ser
                85              90
```